(12) United States Patent
Daniloff et al.

(10) Patent No.: US 7,273,896 B2
(45) Date of Patent: Sep. 25, 2007

(54) COMPOSITIONS AND METHODS OF USING A TRANSIENT COLORANT

(75) Inventors: George Y. Daniloff, Mountain View, CA (US); John R. Daniels, Pacific Palisades, CA (US)

(73) Assignee: Angiotech Pharmaceuticals (US), Inc., North Bend, WA (US)

( * ) Notice: Subject to any disclaimer, the term of this patent is extended or adjusted under 35 U.S.C. 154(b) by 3 days.

(21) Appl. No.: 10/412,710

(22) Filed: Apr. 10, 2003

(65) Prior Publication Data

US 2004/0202625 A1    Oct. 14, 2004

(51) Int. Cl.
C08F 2/46 (2006.01)

(52) U.S. Cl. .............................. 522/86; 522/84; 522/85; 522/74; 522/71; 522/72; 522/81; 522/87; 522/88; 522/104; 522/106; 522/107; 522/109; 522/111; 522/110; 522/112; 522/113; 522/114; 522/119; 522/124; 522/123; 522/134; 522/135; 522/142; 522/144; 522/145; 522/149; 522/154; 522/162; 523/113; 523/111; 523/118; 242/426; 242/489; 427/2.1; 427/323; 427/508; 427/2.11; 427/2.13

(58) Field of Classification Search .................. 522/84, 522/85, 86, 71, 72, 74, 81, 87, 88, 89, 90, 522/104, 106, 107, 109–112, 113, 114, 119–124, 522/134–144, 149–154, 162; 523/111, 113, 523/118; 427/2.7, 323, 508; 424/426, 489
See application file for complete search history.

(56) References Cited

U.S. PATENT DOCUMENTS

| | | | |
|---|---|---|---|
| 3,928,272 A | 12/1975 | Brancato et al. | |
| 4,507,413 A | 3/1985 | Thoma et al. | |
| 5,124,182 A | 6/1992 | Kubo et al. | |
| 5,162,430 A | 11/1992 | Rhee et al. | |
| 5,209,776 A * | 5/1993 | Bass et al. ................ 106/124.1 | |
| 5,324,775 A | 6/1994 | Rhee et al. | |
| 5,328,955 A | 7/1994 | Rhee et al. | |
| 5,410,016 A * | 4/1995 | Hubbell et al. ............. 528/354 |
| 5,425,824 A * | 6/1995 | Marwick ..................... 156/64 |
| 5,573,934 A * | 11/1996 | Hubbell et al. ............. 435/177 |
| 5,580,923 A * | 12/1996 | Yeung et al. ............... 525/54.1 |
| 5,614,587 A | 3/1997 | Rhee et al. | |
| 6,239,190 B1 * | 5/2001 | Wilkinson et al. ............ 522/87 |
| 6,258,872 B1 * | 7/2001 | Stedronsky ................. 523/118 |
| 2001/0003126 A1 | 6/2001 | Rhee et al. | |
| 2002/0042473 A1 | 4/2002 | Trollsas et al. | |
| 2002/0082636 A1 | 6/2002 | Sawhney et al. | |
| 2002/0091229 A1 | 7/2002 | Hubbell et al. | |
| 2006/0147409 A1 | 7/2006 | Pathak et al. | |

FOREIGN PATENT DOCUMENTS

| | | | |
|---|---|---|---|
| EP | 0 486 020 | | 5/1992 |
| EP | 0732109 A1 | | 9/1996 |
| JP | 2002-088336 | | 3/2002 |
| WO | WO92/02238 | * | 2/1992 |
| WO | WO92/09639 | | 6/1992 |
| WO | WO93/11751 | | 6/1993 |
| WO | WO 00/09087 | | 2/2000 |
| WO | WO 00/33764 | | 6/2000 |

OTHER PUBLICATIONS

West et al. (1995), "Comparison of Covalently and Physically Cross-Linked Polyethylene Glycol-Based Hydrogels for the Prevention of Postoperative Adhesions in a Rat Model," *Biomaterials* 16:1153-1156.

* cited by examiner

*Primary Examiner*—Sanza L. McClendon
(74) *Attorney, Agent, or Firm*—Mintz, Levin, Cohn, Ferris, Glovsky and Popeo PC

(57) ABSTRACT

This invention relates generally to compositions and systems for forming biomaterials containing a transient colorant for visualizing tissue or surgical materials coated with such biomaterials, to methods of using such compositions as bioadhesives, for tissue augmentation, in the prevention of surgical adhesions, for coating surfaces of synthetic implants, as drug delivery matrices, for ophthalmic applications, and in other applications.

61 Claims, No Drawings

COMPOSITIONS AND METHODS OF USING A TRANSIENT COLORANT

TECHNICAL FIELD

This invention relates generally to compositions and systems for forming biomaterials containing a transient colorant. More particularly, this invention relates to use of these biomaterials for visualizing tissue or surgical materials coated with such biomaterials. The invention also relates to methods of using such compositions as bioadhesives, for tissue augmentation, in the prevention of surgical adhesions, for coating surfaces of synthetic implants, as drug delivery matrices, for ophthalmic applications, and in other applications, as discussed herein and/or as appreciated by one of ordinary skill in the art.

BACKGROUND OF THE INVENTION

A number of biodegradable polymeric materials have been adapted for surgical use, and for controlled release of bioactive substances. Polymeric and pre-polymeric materials that may be optionally cross-linked that do not comprise a colorant have been used to prevent post-operative surgical adhesions. Examples of such polymers are set forth below.

U.S. Pat. No. 5,162,430 to Rhee et al., discloses collagen-synthetic polymer conjugates prepared by covalently binding collagen to synthetic hydrophilic polymers such as various derivatives of polyethylene glycol.

U.S. Pat. No. 5,324,775 to Rhee et al., discloses various insert, naturally occurring, biocompatible polymers (such as polysaccharides) covalently bound to synthetic, non-immunogenic, hydrophilic polyethylene glycol polymers.

U.S. Pat. No. 5,328,955 to Rhee et al., discloses various activated forms of polyethylene glycol and various linkages which can be used to produce collagen-synthetic polymer conjugates having a range of physical and chemical properties.

EP 0732109A1 to Rhee, discloses a crosslinked biomaterial composition that is prepared using a hydrophobic crosslinking agent, or a mixture of hydrophilic and hydrophobic crosslinking agents. Preferred hydrophobic crosslinking agents include any hydrophobic polymer that contains, or can be chemically derivatized to contain, two or more succinimidyl groups.

U.S. Pat. No. 5,580,923 to Yeung et al., discloses a composition useful in the prevention of surgical adhesions comprising a substrate material and an anti-adhesion binding agent; where the substrate material preferably comprises collagen and the binding agent preferably comprises at least one tissue-reactive functional group and at least one substrate-reactive functional group.

U.S. Pat. No. 5,614,587 to Rhee et al., discloses bioadhesive compositions comprising collagen crosslinked using a multifunctionally activated synthetic hydrophilic polymer, as well as methods of using such compositions to effect adhesion between a first surface and a second surface, wherein at least one of the first and second surfaces is preferably a native tissue surface.

Japanese Patent Publication No. 2002-088336 to Yokoyama et al. discloses a composition used for temporary adhesion of a lens material to a support, to mount the material on a machining device, comprising a mixture of polyethylene glycol, having an average molecular weight in the range of 1000-5000, and poly-N-vinylpyrrolidone, having an average molecular weight in the range of 30,000-200,000.

West and Hubbell, Biomaterials (1995) 16:1153-1156, disclose the prevention of post-operative adhesions using a photopolymerized polyethylene glycol-co-lactic acid diacrylate hydrogel and a physically crosslinked polyethylene glycol-co-polypropylene glycol hydrogel, POLOXAMER 407®.

A polymeric composition that includes a permanent colorant has also been reported, e.g., WO 00/09087 to Sawhney, which relates to hydrogel biomaterials that may also include a permanent colorant. Such a permanent colorant can be generated in situ or one permanent color may be changed to a different permanent color by a chemical reaction after application of the biomaterial. While such permanently colored biomaterials can be helpful to a surgeon in locating where a composition or prosthesis is located at a surgical site, they can also hinder or obliterate the visibility of tissue to which the colored materials have been applied. During surgical procedures, such colored biomaterials can lessen a surgeon's ability to easily and quickly identify bleeding at a surgical site or may lessen a surgeon's ability to view anatomical structures that may be covered by such biomaterials.

Accordingly, there is a need for improved biocompatible compositions that overcome the difficulties described above, and provide improved visibility during surgical procedures.

Each publication cited above is incorporated herein by reference to describe and to disclose the subject matter for which it is cited.

SUMMARY OF THE INVENTION

Accordingly, in one aspect of the invention, a transiently visible pharmaceutical formulation, surgical composition or prosthesis coating is provided that is biocompatible and non-immunogenic and has utility in a host of different contexts, e.g., in bioadhesion, biologically active agent delivery, tissue augmentation, surgical sealants, surgical adhesion barriers, and other applications. The biocompatible composition or formulation includes:

(i) a polymeric material, a pre-polymeric material capable of polymerizing to form a polymeric material upon excitation (such as excitation by intense visible light, laser stimulation, ultraviolet light, or electrical current), or a mixture thereof and (ii) a transient colorant that is a substantially invisible colorant until excited, and may be selected from the group consisting of a dye, pigment, luminescent agent, or a mixture thereof, wherein the colorant is capable of being trapped within a polymeric material, is capable of being bound to a polymeric material, or is capable of being bound to a pre-polymeric material that is capable of polymerizing to form a polymeric material upon excitation. The transient colorant is capable of being rendered transiently visible in an excited state as result of being excited by intense visible light, laser stimulation, ultraviolet light, electrical current, and the like. The pre-polymeric material is capable of polymerizing as a result of being excited by a pH change, moisture, intense visible light, electrical current, ultraviolet light, laser stimulation, an initiator, a catalyst, a combination of two or more of the above, and the like.

In another aspect, the polymeric material of the composition may be in the form of a homopolymer, copolymer, terpolymer, or the like. The pre-polymeric material may be in situ polymerizable, and the pre-polymeric material may be a single monomer, or it may be mixture of two or more monomers. Also, small molecule compounds having multiple reactive groups, such as diethanolamine and the like, may also be utilized as a monomer. The pre-polymeric material may optionally include polyethylene oxide monomer, and the pre-polymer, the polymer, or both the pre-polymer and polymer may be capable of cross-linking. The colorant of the composition may optionally be bound to a polymer or pre-polymer by ionic or covalent bonding.

In another aspect the invention is a composition including a colorant (dye, pigment, or luminescent agent) that is substantially colorless until it is excited by an excitation source and is substantially immediately reverted to a substantially colorless state when the excitation source is removed. Examples of excitation sources for rendering the colorant transiently visible are intense visible light, laser stimulation, ultraviolet light, electrical current, and the like.

In a further aspect, the colorant is a dye or pigment that includes a chromophore or a luminescent agent. One luminescent agent is a fluorescent dye, particularly dyes that have an excitation wavelength from 300 nm to 700 nm. Examples of acceptable fluorescent dyes are fluorescein, carboxyfluorescein, eosin, erythrosine, a TEXAS RED® dye (rhodamine dyes containing a julolidine ring structure), rhodamine, coumarin, BODIPY® dye (4,4-difluoro-4-bora-3a,4a-diaza-s-indacene fluorophores), or a combination thereof. The colorant may be modified or conjugated with a moiety that enhances the colorant's binding or absorption onto a biological tissue surface.

In one aspect the invention provides a composition that is capable of in-situ polymerization, and the composition comprises a transient colorant selected from the group consisting of a dye, pigment, luminescent agent, and a mixture thereof, wherein the composition further includes at least two cross-linkable polymeric or pre-polymeric components, and wherein the colorant is capable of being bound to at least one of the components by covalent or ionic bonding.

In still another aspect, the invention is a composition that is capable of preventing surgical adhesion during surgical procedures.

In yet another aspect, the invention is a composition that is capable of marking, labeling or otherwise rendering tissue surfaces visible, when the composition is applied to tissues prior to or during surgical procedures, wherein the tissue surfaces are rendered visible by observing or detecting fluorescent light or color emitted by the excited colorant of the composition.

In another aspect, the invention is a method of visualizing, marking, or labeling a tissue surface during a surgical procedure comprising (a) applying to a tissue surface a biocompatible composition comprising:
  (i) a polymeric material, a pre-polymeric material capable of polymerizing to form a polymeric material upon excitation, or a mixture thereof, and
  (ii) a transient colorant selected from the group consisting of a dye, pigment, luminescent agent, and a mixture thereof; wherein said colorant is capable of being trapped within a polymeric material, is capable of being bound to a polymeric material, or is capable of being bound to a pre-polymeric material that is capable of polymerizing to form a polymeric material upon excitation, and (b) applying an excitation source to the composition sufficient to render said colorant visible. The surgical procedure may be invasive surgery, or may be minimally invasive. A minimally invasive surgical procedure may include a laporoscopic procedure step. The composition may be applied to a surgical site in bulk or may be applied as a thin layer. The thin layer may be a film that adheres to the tissue surface. Such a thin layer may include a polyethylene oxide polymer, or the like.

In yet another aspect the invention provides a method of visualizing, marking, or labeling a tissue surface or a prosthetic surface during a surgical procedure comprising applying to the surface of a tissue, surgical implant, or prosthesis the composition as described above, wherein the pharmaceutical formulation, surgical or prosthesis coating composition is biocompatible and non-immunogenic and has utility in a host of different contexts, e.g., in bioadhesion, biologically active agent delivery, tissue augmentation, surgical sealants, surgical adhesion barriers, and other applications. In one such method the composition is substantially transparent and essentially colorless until an excitation source (such as a light source) is applied to the composition under conditions that cause light fluorescence emissions from a transiently visible fluorescent dye in the composition.

In a further aspect, the invention is an improved transiently visible barrier or drug delivery system that adheres strongly to a tissue surface to which it is applied. The system may be very compliant to movement and be capable of conforming to a three-dimensional structure of a tissue surface as tissue bends and deforms during healing processes.

In another aspect, a transiently visible barrier or drug delivery system composition is formed as a polymeric coating on tissue surfaces by applying a polymerizable monomers, or mixture of monomers composition, to the surface and polymerizing in situ the composition with an polymerizing excitation source. The polymerized coating may be compliant to movement, biodegradable and biocompatible, and the coating can be designed with selected properties of compliancy and elasticity for different surgical and therapeutic applications.

In yet another aspect, the composition or method may comprise at least one additional active component such as a polymer (e.g., may be used to modulate the mechanical properties of the composition), a small molecule therapeutic agent, a biopolymer (e.g., collagen that may enhance tissue regeneration) and biological materials such as tissue, cells, fluids, or a mixture thereof.

In other aspects of the invention, methods for preparing and using the aforementioned compositions also provided. Methods of using the compositions encompassed by the present invention include drug delivery methods, use in bioadhesion, delivery of cells and genes, tissue augmentation, prevention of adhesions following surgery or injury, and implant coating. Other methods of use are also within the scope of the invention, as will be described below.

DETAILED DESCRIPTION OF THE INVENTION

The invention is directed to a versatile biocompatible composition not previously disclosed or envisioned by those in the biomaterial field. The composition is comprised of biomaterials and includes a transiently visible colorant, such as a fluorescent dye. Such a composition has a variety of uses, e.g., as a sealant, a bioadhesive, a surgical glue, as a drug delivery platform, as a coating for cells, tissue, or implants, etc. All components of the composition are biocompatible, are not systemically immunogenic, and do not leave at the site of administration undesired toxic, inflammatory or immunogenic reaction products. Compositions may be selected to promote a desired amount of local inflammation or to otherwise have local effects that may lead to desired scar tissue generation. In one embodiment, the composition is not subject to enzymatic cleavage by matrix metalloproteinases such as collagenase, and is therefore not readily degradable in vivo.

In one embodiment, the composition is substantially transparent and colorless until it is excited and becomes transiently visible. Further, the composition may be readily tailored, in terms of the selection and quantity of each component, to enhance certain properties, e.g., compression strength, swellability, tack, hydrophilicity, optical clarity, and the like, as well as to provide transient visibility.

Before describing the present invention in detail, it is to be understood that unless otherwise indicated this invention is not limited to particular compositional forms, or methods of use, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, "a transient colorant" refers not only to a single transparent colorant compound but also to a combination of two or more different colorant compounds component, "a polymeric material" refers to a combination of two or more polymers as well as to a single polymer, and the like.

Unless defined otherwise, all technical and scientific terms used herein have the meaning commonly understood by one of ordinary skill in the art to which the invention pertains. Although any methods and materials similar or equivalent to those described herein may be useful in the practice or testing of the present invention, preferred methods and materials are described below. All patents, patent applications and other publications mentioned herein are incorporated herein by reference. Specific terminology of particular importance to the description of the present invention is defined below.

The term "crosslinked" herein refers to a composition containing intermolecular crosslinks and optionally intramolecular crosslinks as well, arising from the formation of covalent bonds. Covalent bonding between two crosslinkable components may be direct, in which case an atom in one component is directly bound to an atom in the other component, or it may be indirect, through a linking group. A crosslinked matrix may, in addition to covalent bonds, also include intermolecular and/or intramolecular noncovalent bonds such as hydrogen bonds and electrostatic (ionic) bonds. The term "crosslinkable" refers to a component or compound that is capable of undergoing reaction to form a crosslinked composition.

The terms "nucleophile" and "nucleophilic" refer to a functional group that is electron rich, has an unshared pair of electrons acting as a reactive site, and reacts with a positively charged or electron-deficient site, generally present on another molecule.

The terms "electrophile" and "electrophilic" refer to a functional group that is susceptible to nucleophilic attack, i.e., susceptible to reaction with an incoming nucleophilic group. Electrophilic groups herein are positively charged or electron-deficient, typically electron-deficient.

The term "activated" refers to a modification of an existing functional group to generate or introduce a new reactive functional group from the prior existing functional group, wherein the new reactive functional group is capable of undergoing reaction with another functional group to form a covalent bond. For example, a component containing carboxylic acid (—COOH) groups can be activated by reaction with N-hydroxy-succinimide or N-hydroxysulfosuccinimide using known procedures, to form an activated carboxylate (which is a reactive electrophilic group), i.e., an N-hydroxysuccinimide ester or an N-hydroxysulfosuccinimide ester, respectively. In another example, carboxylic acid groups can be activated by reaction with an acyl halide, e.g., an acyl chloride, again using known procedures, to provide an activated electrophilic group in the form of an anhydride.

The terms "hydrophilic" and "hydrophobic" are generally defined in terms of a partition coefficient P, which is the ratio of the equilibrium concentration of a compound in an organic phase to that in an aqueous phase. A hydrophilic compound has a log P value less than 1.0, typically less than about −0.5, where P is the partition coefficient of the compound between octanol and water, while hydrophobic compounds will generally have a log P greater than about 3.0, typically greater than about 5.0. Preferred crosslinkable components herein are hydrophilic, although as long as the crosslinkable composition as a whole contains at least one hydrophilic component, crosslinkable hydrophobic components may also be present.

The term "biocompatible" in describing an item, such as when referring to a component, a starting material, an agent of a composition, a reaction product, or a metabolite, means that undesired toxic, inflammatory and immunogenic effects are substantially absent. However, a biocompatible material may be selected to have desired local effects that might be inflammatory, immunogenic, or the like, which could lead to the promotion or generation of local scarring, or some other desired therapeutic effect.

The term "polymeric material" is used not only in the conventional sense to refer to polymers composed of repeating monomer units, including homopolymers, block copolymers, random copolymers, and graft copolymers, but also, as indicated in published patent application US2001/0003126A to Rhee, et al., may also refer to polyfunctional small molecules that do not contain exactly repeating monomer units but are "polymeric" in the sense of being "polyfunctional," i.e., containing two or more functional groups. All suitable polymers herein are biocompatible and do not lead to toxic or systemic immunogenic effects. In one embodiment, such polymers will be readily biodegradable, e.g., adhesion preventatives. In another embodiment, the polymers are intended to be implants that are essentially non-degradable in vivo over a period of at least several months.

The term "monomer" is used herein to include classically understood monomer units that produce polymers composed of regularly repeating monomeric residues, however, it will be appreciated that when the term "monomer" is used, difunctional and polyfunctional small molecules are included as indicated in published patent application US2001/0003126A to Rhee, et al. Such moieties include, by way of example: the difunctional electrophiles disuccinimidyl suberate (DSS), bis(sulfosuccinimidyl) suberate (BS$^3$), dithiobis(succinimidylpropionate) (DSP), bis(2-succinimidooxy-carbonyloxy) ethyl sulfone (BSOCOES), 3,3'-dithiobis(sulfosuccinimidylpropionate (DTSSP); and the di- and polyfunctional nucleophiles ethylenediamine ($H_2N-CH_2-CH_2-NH_2$), tetramethylene diamine ($H_2N-[CH_2]_4-NH_2$), pentamethylene diamine (cadaverine) ($H_2N-[CH_2]_5-NH_2$), hexamethylene diamine ($H_2N-[CH_2]_6-NH_2$), bos(2-aminoethyl)amine ($HN-[CH_2-CH_2-NH_2]_2$), and tris (2-aminoethyl)amine ($N-[CH_2-CH_2-NH_2]_3$).

The term "synthetic" to refer to various polymers herein is intended to mean "chemically synthesized." Therefore, a synthetic polymer in the present compositions may have a molecular structure that is identical to a naturally occurring polymer, but the polymer per se, as incorporated in the compositions of the invention, has been chemically synthesized in the laboratory or industrially. "Synthetic" polymers also include semi-synthetic polymers, i.e., naturally occurring polymers, obtained from a natural source, that have been chemically modified in some way. Generally, however, the synthetic polymers herein are purely synthetic, i.e., they are neither semi-synthetic nor have a structure that is identical to that of a naturally occurring polymer.

The term "synthetic hydrophilic polymer" as used herein refers to a synthetic polymer composed of molecular segments that render the polymer as a whole "hydrophilic," as defined above. Preferred polymers are highly pure or are purified to a highly pure state such that the polymer is or is treated to become pharmaceutically pure. Most hydrophilic polymers can be rendered water soluble by incorporating a sufficient number of oxygen (or less frequently nitrogen) atoms available for forming hydrogen bonds in aqueous solutions. Hydrophilic polymers useful herein include, but are not limited to: polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxy-ethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropyl-acrylamide); poly(olefinic alcohol)s such as poly(vinyl alcohol); poly(N-vinyl lactams) such as poly(vinyl pyrrolidone), poly(N-vinyl caprolactam), and copolymers thereof; polyoxazolines, including poly(methyloxazoline) and poly(ethyloxazoline); and polyvinylamines.

Hydrophobic polymers, including low molecular weight polyfunctional species, can also be used in the crosslinkable compositions of the invention. Hydrophobic polymers preferably contain, or can be derivatized to contain, two or more electrophilic groups, such as succinimidyl groups, most preferably, two, three, or four electrophilic groups. Generally, "hydrophobic polymers" herein contain a relatively small proportion of oxygen and/or nitrogen atoms. Preferred hydrophobic polymers for use in the invention generally have a carbon chain that is no longer than about 14 carbons. Polymers having carbon chains substantially longer than 14 carbons generally have very poor solubility in aqueous solutions and, as such, have very long reaction times when mixed with aqueous solutions of synthetic polymers containing multiple nucleophilic groups.

The term "collagen" as used herein refers to all forms of collagen, including those, which have been processed or otherwise modified (collagen may also be referred to generally as a biopolymer even if collagen is a synthetic polymer). Preferred collagens are treated to remove the immunogenic telopeptide regions ("atelopeptide collagen"), are soluble, and may be in fibrillar or non-fibrillar form. Type I collagen is best suited to most applications involving bone or cartilage repair. However, other forms of collagen are also useful in the practice of the invention, and are not excluded from consideration here. Collagen crosslinked using heat, radiation, or chemical agents such as glutaraldehyde may also be used to form particularly rigid crosslinked compositions. Collagen crosslinked using glutaraldehyde or other (nonpolymer) linking agents is typically referred to herein as "GAX" while collagen crosslinked using heat and/or radiation is termed "HRX." Collagen used in connection with the preferred embodiments of the invention is in a pharmaceutically pure form such that it can be incorporated into a human body for the intended purpose.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weights indicates that the average molecular weight may be any value between the limits specified, and may include molecules outside those limits. Thus, a molecular weight range of about 800 to about 20,000 indicates an average molecular weight of at least about 800, ranging up to about 20 kDa.

The term "effective amount" refers to the amount of composition required in order to obtain the effect desired. Thus, a "tissue growth-promoting amount" of a composition refers to the amount needed in order to stimulate tissue growth to a detectable degree. Tissue, in this context, includes connective tissue, bone, cartilage, epidermis and dermis, blood, and other tissues. The actual amount that is determined to be an effective amount will vary depending on factors such as the size, condition, sex and age of the patient and can be more readily determined by the caregiver.

The term "in situ" as used herein means at the site of administration. Thus, the injectable reaction mixture compositions are injected or otherwise applied to a specific site within a patient's body, e.g., a site in need of augmentation or visualization, and the composition may be allowed to cross-link at the site of injection. An excitation source may be applied to visualize the composition before, during or after polymerization. On group of suitable sites will generally be intradermal or subcutaneous regions for augmenting dermal support, at a bone fracture site for bone repair, within sphincter tissue for sphincter augmentation (e.g., for restoration of continence), within a wound or suture, to promote tissue regrowth; and within or adjacent to vessel anastomoses, to promote vessel regrowth. Another group of suitable sites for composition application is wound areas, surgical areas, areas adjacent to surgical sites, and the like.

The term "aqueous medium" includes solutions, suspensions, dispersions, colloids, and the like containing water.

The term "substantially immediately" means within less than five minutes, preferably within less than two minutes, and the term "immediately" means within less than one minute, preferably within less than 30 seconds. The term "instantaneously" means something that occurs at once, i.e., in less than 15 seconds.

The terms "essentially colorless" and "substantially colorless" are used interchangeably and mean that the composition, prosthesis or other structure does not contain enough colorant to hinder easy visualization of tissue or anatomy when looking through the composition, prosthesis or other structure in behind the composition, prosthesis or other structure.

The terms "essentially transparent" and "substantially transparent" are used interchangeably and mean that that a viewer can see through a composition, prosthesis or other structure to easily visualize tissue or anatomy that is in behind such a composition, prosthesis or other structure.

The term "transiently visible" means that a substance comprising a transient colorant only produces the observable color change or visible fluorescence when an visual activation source such as intense light, radiation, electric current, UV light, and the like is applied to that substance to cause it to produce florescence or a temporary color state. In a preferred example, a transiently visible substance is essentially transparent and colorless until an excitation source is applied that causes visible fluorescence of the substance or a color change.

The term "transient colorant" means that a substance such as a dye, pigment, or luminescent agent only has an observable color change or visible fluorescence when excited. Typically, this occurs when a visual activation source such as radiation, electric current, UV light, and the like is applied to that substance to produce either florescence or some other temporarily visible state, such as a color or color change. In a preferred aspect the transient colorant is also essentially transparent and colorless until an excitation source is applied. The colorant may be a stand-alone compound, or it may be bound to another chemical structure, including a pre-polymeric or polymeric structure.

The terms "active agent," and "biologically active agent" are used interchangeably herein to refer to a chemical material or compound suitable for administration to a patient and that induces a desired effect. The terms include agents that are therapeutically effective as well as prophylactically effective. Also included are derivatives and analogs of those compounds or classes of compounds specifically mentioned that also induce the desired effect.

The term "hydrogel" is used in the conventional sense to refer to water-swellable polymeric matrices that can absorb a substantial amount of water to form elastic gels, wherein "matrices" are three-dimensional networks of macromolecules held together by covalent or noncovalent crosslinks. Upon placement in an aqueous environment, dry hydrogels swell to the extent allowed by the degree of cross-linking.

With regard to nomenclature pertinent to molecular structures, the following definitions apply:

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups. "Alkylene," "lower alkylene" and "substituted alkylene" refer to divalent alkyl, lower alkyl, and substituted alkyl groups, respectively.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom. The terms "arylene" and "substituted arylene" refer to divalent aryl and substituted aryl groups as just defined.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. If not otherwise indicated, "hydrocarbyl" indicates unsubstituted hydrocarbyl, substituted hydrocarbyl, heteroatom-containing hydrocarbyl, and substituted heteroatom-containing hydrocarbyl. Unless otherwise indicated, the terms "hydrocarbyl" and "hydrocarbylene" include substituted hydrocarbyl and substituted hydrocarbylene, heteroatom-containing hydrocarbyl and heteroatom-containing hydrocarbylene, and substituted heteroatom-containing hydrocarbyl and substituted heteroatom-containing hydrocarbylene, respectively.

By "substituted" as in "substituted hydrocarbyl," "substituted alkyl," and the like, as alluded to in some of the aforementioned definitions, is meant that in the hydrocarbyl, alkyl, or other moiety, at least one hydrogen atom bound to a carbon atom is replaced with one or more substituents that are functional groups such as alkoxy, hydroxy, halo, nitro, and the like. Unless otherwise indicated, it is to be understood that specified molecular segments can be substituted with one or more substituents that do not compromise a compound's utility. For example, "succinimidyl" is intended to include unsubstituted succinimidyl as well as sulfosuccinimidyl and other succinimidyl groups substituted on a ring carbon atom, e.g., with alkoxy substituents, polyether substituents, or the like.

II. Transient Colorants

The transient colorant may be a dye, pigment, luminescent agent, and a mixture thereof, and in a preferred embodiment, the colorant may be dye or pigment that includes a chromophore or a luminescent agent. All that is necessary is that the colorant be capable of being rendered transiently visible in an excited state. One luminescent agent useful as a transient colorant is a fluorescent dye, particularly preferred is dyes that have an excitation wavelength from 300 nm to 700 nm. Examples of acceptable fluorescent dyes are fluorescein, carboxyfluorescein, eosin, erythrosine, a Texas Red dye, rodamine, coumarin, BODIPY dye, or a combination thereof. The colorant may be modified or conjugated with a moiety that enhances the colorant's binding or absorption onto a biological tissue surface. In one aspect the invention provides a composition that is capable of in-situ polymerization, and the colorant is capable of being bound to at least one of the components by covalent or ionic bonding.

III. Biocompatible Polymeric Compositions

In accordance with the present invention, the composition and method may involve a polymer composition that comprises a transient colorant. Acceptable polymers may be hydrophilic, hydrophobic, mixed hydrophilic and hydrophobic, cross-linkable or non-crosslinkable, biopolymers, or non-biopolymers. Polymers may be homopolymers, copolymers, terpolymers, or other mixed polymers, wherein such polymers may be present in their polymeric form in the composition or may be generated in situ, cross-linked in situ, or both generated and cross-linked in situ. Some examples of acceptable polymers that may be cross-linked are described in the following patents U.S. Pat. No. 5,527,864 to Suggs et al., U.S. Pat. No. 5,160,745 to De Luca et al. U.S. Pat. No. 5,100,992 to Cohn et al., U.S. Pat. No. 4,938,763 to Dunn et al., U.S. U.S. Pat. No. 4,826,945 to Cohn et al., U.S. Pat. No. 4,741,872 to De Luca et al., and U.S. Pat. No. 4,511,478 to Nowinski et al. One embodiment contains a minimum of three components, each of which participates in a reaction that results in a cross-linked matrix. The components of the optionally crosslinkable composition may be selected so that the mixture or a crosslinking reaction gives rise to a biocompatible, nonimmunogenic matrix useful in a variety of contexts, including as a sealant, for adhesion, for biologically active agent delivery, tissue augmentation, coating for implants, cells or tissue, and for other similar types of applications.

A. Hydrophilic Polymers and Optional "Activation" Thereof

A "hydrophilic polymer" as used herein refers to a synthetic polymer having an average molecular weight and composition effective to render the polymer "hydrophilic" as defined in about definitions sections. Synthetic hydrophilic polymers useful herein include, but are not limited to: polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, poly(methacrylic acid, poly(hydroxyethyl-methacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropylacrylamide); poly(olefinic alcohol)s such as poly(vinyl alcohol); poly(N-vinyl lactams) such as poly(vinyl pyrrolidone), poly(N-vinyl caprolactam), and copolymers thereof; polyoxazolines, including poly(methyloxazoline) and poly(ethyloxazoline); and polyvinylamines. It must be emphasized that the aforementioned list of polymers is not exhaustive, and a variety of other synthetic hydrophilic polymers may be used, as will be appreciated by those skilled in the art.

The synthetic hydrophilic polymer may be a homopolymer, a block copolymer, a random copolymer, or a graft copolymer. In addition, the polymer may be linear or branched, and if branched, may be minimally to highly branched, dendrimeric, hyperbranched, or a star polymer. The polymer may include biodegradable segments and blocks, either distributed throughout the polymer's molecular structure or present as a single block, as in a block copolymer. Biodegradable segments are those that degrade so as to break covalent bonds. Typically, biodegradable segments are segments that are hydrolyzed in the presence of water and/or enzymatically cleaved in situ. Biodegradable segments may be composed of small molecular segments such as ester linkages, anhydride linkages, ortho ester linkages, ortho carbonate linkages, amide linkages, phosphonate linkages, etc. Larger biodegradable "blocks" will generally be composed of oligomeric or polymeric segments incorporated within the hydrophilic polymer. Illustrative oligomeric and polymeric segments that are biodegradable include, by way of example, poly(amino acid) segments, poly(orthoester) segments, poly(orthocarbonate) segments, and the like.

Although a variety of different synthetic hydrophilic polymers can be used in the present compositions, as indicated above, preferred synthetic hydrophilic polymers are polyethylene glycol (PEG) and polyglycerol (PG), particularly highly branched polyglycerol. Various forms of PEG are extensively used in the modification of biologically active molecules because PEG lacks toxicity, antigenicity, and immunogenicity (i.e., is biocompatible), can be formulated so as to have a wide range of solubilities, and does not typically interfere with the enzymatic activities and/or conformations of peptides. A particularly preferred synthetic hydrophilic polymer for certain applications is a polyethylene glycol (PEG) having a molecular weight within the range of about 100 to about 100,000 mol. wt., although for highly branched PEG, far higher molecular weight polymers can be employed—up to 1,000,000 or more—providing that biodegradable sites are incorporated ensuring that all degradation products will have a molecular weight of less than about 30,000. For most PEGs, however, the preferred molecular weight is about 1,000 to about 20,000 mol. wt., more preferably within the range of about 7,500 to about 20,000 mol. wt. Most preferably, the polyethylene glycol has a molecular weight of approximately 10,000 mol. wt.

Other suitable synthetic hydrophilic polymers include chemically synthesized polypeptides, particularly polynucleophilic polypeptides that have been synthesized to incorporate amino acids containing primary amino groups (such as lysine) and/or amino acids containing thiol groups (such as cysteine). Poly(lysine), a synthetically produced polymer of the amino acid lysine (145 MW), is particularly preferred. Poly(lysine)s have been prepared having anywhere from 6 to about 4,000 primary amino groups, corresponding to molecular weights of about 870 to about 580,000. Poly (lysine)s for use in the present invention preferably have a molecular weight within the range of about 1,000 to about 300,000, more preferably within the range of about 5,000 to about 100,000, and most preferably, within the range of about 8,000 to about 15,000. Poly(lysine)s of varying molecular weights are commercially available from Peninsula Laboratories, Inc. (Belmont, Calif.).

Naturally occurring hydrophilic polymers include, but are not limited to: proteins such as collagen, fibronectin, albumins, globulins, fibrinogen, fibrin and thrombin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; and activated polysaccharides such as dextran and starch derivatives. Collagen and glycosaminoglycans are preferred naturally occurring hydrophilic polymers for use herein.

In general, collagen from any source may be used in the compositions of the invention; for example, collagen may be extracted and purified from human or other mammalian source, such as bovine or porcine corium and human placenta, or may be recombinantly or otherwise produced. The preparation of purified, substantially non-antigenic collagen in solution from bovine skin is well known in the art. Commonly owned U.S. Pat. No. 5,428,022, issued Jun. 27, 1995 to Palefsky et al., discloses methods of extracting and purifying collagen from the human placenta. Commonly owned U.S. Pat. No. 5,667,839, issued Sep. 16, 1997 to Berg, discloses methods of producing recombinant human collagen in the milk of transgenic animals, including transgenic cows. The term "collagen" or "collagen material" as used herein refers to all forms of collagen, including those that have been processed or otherwise modified.

Collagen of any type, including, but not limited to, types I, II, III, IV, or any combination thereof, may be used in the compositions of the invention, although type I is generally preferred. Either atelopeptide or telopeptide-containing collagen may be used; however, when collagen from a source, such as bovine collagen, is used, atelopeptide collagen is generally preferred, because of its reduced immunogenicity compared to telopeptide-containing collagen.

Collagen that has not been previously crosslinked by methods such as heat, irradiation, or chemical crosslinking agents is preferred for use in the compositions of the invention, although previously crosslinked collagen may be used. Non-crosslinked atelopeptide fibrillar collagen is commercially available from Angiotech Pharmaceuticals (US). Inc. (North Bend, Wash.) at collagen concentrations of 35 mg/ml and 65 mg/ml under the trademarks ZYDERM® I Collagen and ZYDERM® II Collagen, respectively. Glutaraldehyde-crosslinked atelopeptide fibrillar collagen is commercially available from Angiotech Pharmaceuticals (US), Inc. at a collagen concentration of 35 mg/ml under the trademark ZYPLAST®.

Collagens for use in the present invention are generally, although not necessarily, in aqueous suspension at a concentration between about 20 mg/ml to about 120 mg/ml, preferably between about 30 mg/ml to about 90 mg/ml.

Although intact collagen is preferred, denatured collagen, commonly known as gelatin, can also be used in the compositions of the invention. Gelatin may have the added benefit of being degradable faster than collagen.

Because of its tacky consistency, nonfibrillar collagen is generally preferred for use in compositions of the invention that are intended for use as bioadhesives. The term "nonfibrillar collagen" refers to any modified or unmodified collagen material that is in substantially nonfibrillar form at pH 7, as indicated by optical clarity of an aqueous suspension of the collagen.

Collagen that is already in nonfibrillar form may be used in the compositions of the invention. As used herein, the term "nonfibrillar collagen" is intended to encompass collagen types that are nonfibrillar in native form, as well as collagens that have been chemically modified such that they are in nonfibrillar form at or around neutral pH. Collagen types that are nonfibrillar (or microfibrillar) in native form include types IV, VI, and VII.

Chemically modified collagens that are in nonfibrillar form at neutral pH include succinylated collagen and methylated collagen, both of which can be prepared according to the methods described in U.S. Pat. No. 4,164,559, issued Aug. 14, 1979, to Miyata et al., which is hereby incorporated by reference in its entirety. Due to its inherent tackiness, methylated collagen is particularly preferred for use in bioadhesive compositions, as disclosed in commonly owned U.S. Pat. No. 5,614,587 to Rhee et al.

Collagens for use in the crosslinkable compositions of the present invention may start out in fibrillar form, then rendered nonfibrillar by the addition of one or more fiber disassembly agent. The fiber disassembly agent must be present in an amount sufficient to render the collagen substantially nonfibrillar at pH 7, as described above. Fiber disassembly agents for use in the present invention include, without limitation, various biocompatible alcohols, amino acids, inorganic salts, and carbohydrates, with biocompatible alcohols being particularly preferred. Preferred biocompatible alcohols include glycerol and propylene glycol. Non-biocompatible alcohols, such as ethanol, methanol, and isopropanol, are not preferred for use in the present invention, due to their potentially deleterious effects on the body of the patient receiving them. Preferred amino acids include arginine. Preferred inorganic salts include sodium chloride and potassium chloride. Although carbohydrates, such as various sugars including sucrose, may be used in the practice of the present invention, they are not as preferred as other types of fiber disassembly agents because they can have cytotoxic effects in vivo.

Because it is opaque and less tacky than nonfibrillar collagen, fibrillar collagen is less preferred for use in bioadhesive compositions. However, as disclosed in commonly owned, U.S. Pat. No. 5,614,587 to Rhee et al., fibrillar collagen, or mixtures of nonfibrillar and fibrillar collagen, may be preferred for use in adhesive compositions intended for long-term persistence in vivo, if optical clarity is not a requirement.

For those compositions intended to be used in tissue augmentation, fibrillar collagen is preferred because it tends to form stronger crosslinked gels having greater long-term persistency in vivo than those prepared using nonfibrillar collagen.

Any of the hydrophilic polymers herein must contain, or be activated to contain, functional groups, i.e., nucleophilic or electrophilic groups, which enable crosslinking. Activation of PEG is discussed below; it is to be understood, however, that the following discussion is for purposes of illustration and analogous techniques may be employed with other polymers.

With respect to PEG, first of all, various functionalized polyethylene glycols have been used effectively in fields such as protein modification (see Abuchowski et al., Enzymes as Drugs, John Wiley & Sons: New York, N.Y. (1981) pp. 367-383; and Dreborg et al., Crit. Rev. Therap.

Drug Carrier Syst. (1990) 6:315), peptide chemistry (see Mutter et al., The Peptides, Academic: New York, N.Y. 2:285-332; and Zalipsky et al., Int. J. Peptide Protein Res. (1987) 30:740), and the synthesis of polymeric drugs (see Zalipsky et al., Eur. Polym. J. (1983) 19:1177; and Ouchi et al., J. Macromol. Sci. Chem. (1987) A24:1011).

Activated forms of PEG, including multifunctionally activated PEG, are commercially available, and are also easily prepared using known methods. For example, see Chapter 22 of Poly(ethylene Glycol) Chemistry: Biotechnical and Biomedical Applications, J. Milton Harris, ed., Plenum Press, N.Y. (1992); and Shearwater Polymers, Inc. Catalog, Polyethylene Glycol Derivatives, Huntsville, Ala. (1997-1998).

Structures for some specific, tetrafunctionally activated forms of PEG are shown in FIGS. 1 to 10 of commonly owned published patent application US20020042473A1 to Trollsas et al., which are generalized reaction products obtained by reacting the activated PEGs with multi-amino PEGs, i.e., a PEG with two or more primary amino groups. The activated PEGs illustrated have a pentaerythritol (2,2-bis(hydroxymethyl)-1,3-propanediol) core. Such activated PEGs, as will be appreciated by those in the art, are readily prepared by conversion of the exposed hydroxyl groups in the PEGylated polyol (i.e., the terminal hydroxyl groups on the PEG chains) to carboxylic acid groups (typically by reaction with an anhydride in the presence of a nitrogenous base), followed by esterification with N-hydroxysuccinimide, N-hydroxysulfosuccinimide, or the like, to give the polyfunctionally activated PEG.

Activation with succinimidyl groups to convert terminal hydroxyl groups to reactive esters is one technique for preparing a synthetic hydrophilic polymer with electrophilic moieties suitable for reaction with nucleophiles such as primary amines, thiols, and hydroxyl groups. Other activating agents for hydroxyl groups include carbonyldiimidazole and sulfonyl chloride. However, as discussed in part (B) of this section, a wide variety of electrophilic groups may be advantageously employed for reaction with corresponding nucleophiles. Examples of such electrophilic groups include acid chloride groups; anhydrides, ketones, aldehydes, isocyanate, isothiocyanate, epoxides, and olefins, including conjugated olefins such as ethenesulfonyl ($-SO_2CH=CH_2$) and analogous functional groups.

Hydrophilic di- or poly-nucleophilic polymers (multi-amino PEG) are exemplified in published U.S. 20020042473A1 Trollsas et al. as described above. Various forms of multi-amino PEG are commercially available from Shearwater Polymers (Huntsville, Ala.) and from Texaco Chemical Company (Houston, Tex.) under the name "Jeffamine". Multi-amino PEGs useful in the present invention include Texaco's Jeffamine diamines ("D" series) and tri-amines ("T" series), which contain two and three primary amino groups per molecule. Analogous poly(sulfhydryl) PEGs are also available from Shearwater Polymers, e.g., in the form of pentaerythritol poly(ethylene glycol) ether tetra-sulfhydryl (molecular weight 10,000).

B. Hydrophobic Polymers

The compositions of the invention can also include hydrophobic polymers. Polylactic acid and polyglycolic acid are examples of two hydrophobic polymers that can be used. With other hydrophobic polymers, only short-chain oligomers should be used, containing at most about 14 carbon atoms, to avoid solubility-related problems during reaction unless the composition is applied to a wound site and allowed to polymerize or cross-link at the treatment site.

C. Low Molecular Weight Components and Resulting Polymers or Gels

The polymeric or pre-polymeric composition mixture or the above polymers may also comprise a low molecular weight multifunctional compound, i.e., a $C_2$-$C_{14}$ hydrocarbyl group containing zero to 2 heteroatoms selected from N, O, S and combinations thereof. Such compounds can function as cross-linking agents or as a molecular core of a polymer or gel. Such multifunctional small molecule compounds can be substituted with nucleophilic groups or with electrophilic groups. Such compounds may be present in the composition as single unit "monomeric" structures, partially reacted multi-unit structures or as a polymeric/gel component.

When the low molecular weight molecular core is substituted with primary amino groups, the component may be, for example, ethylenediamine ($H_2N-CH_2CH_2-NH_2$), tetramethylenediamine ($H_2N-(CH_4)-NH_2$), pentamethylenediamine (cadaverine) ($H_2N-(CH_5)-NH_2$), hexamethylenediamine ($H_2N-(CH_6)-NH_2$), bis(2-aminoethyl) amine ($HN-[CH_2CH_2-NH_2]_2$), or tris(2-aminoethyl) amine ($N-[CH_2CH_2-NH_2]_3$).

Low molecular weight diols and polyols include trimethylolpropane, di(trimethylol propane), pentaerythritol, and diglycerol, all of which require activation with a base in order to facilitate their reaction as nucleophiles. Such diols and polyols may also be functionalized to provide di- and poly-carboxylic acids, functional groups that are, as noted earlier herein, also useful as nucleophiles under certain conditions. Polyacids for use in the present compositions include, without limitation, trimethylolpropane-based tricarboxylic acid, di(trimethylol propane)-based tetracarboxylic acid, heptanedioic acid, octanedioic acid (suberic acid), and hexadecanedioic acid (thapsic acid), all of which are commercially available and/or readily synthesized using known techniques.

Low molecular weight di- and poly-electrophiles include, for example, disuccinimidyl suberate (DSS), bis(sulfosuccinimidyl) suberate ($BS_3$), dithiobis(succinimidylpropionate) (DSP), bis(2-succinimidooxycarbonyloxy) ethyl sulfone (BSOCOES), and 3,3'-dithiobis(sulfosuccinimidylpropionate (DTSPP), and their analogs and derivatives. The aforementioned compounds are commercially available from Pierce (Rockford, Ill.). Such di- and poly-electrophiles can also be synthesized from di- and polyacids, for example by reaction with an appropriate molar amount of N-hydroxysuccinimide in the presence of DCC. Polyols such as trimethylolpropane and di(trimethylol propane) can be converted to carboxylic acid form using various known techniques, then further derivatized by reaction with NHS in the presence of DCC to produce trifunctionally and tetrafunctionally activated polymers.

IV. Biocompatible Pre-Polymeric Compositions

A. Starting Materials

Pre-polymeric compositions according to the invention may comprise the multifunctional compounds (described above), contain classic monomers capable of polymerizing, or a mixture thereof in addition to the transient colorant. Additionally, the pre-polymeric compositions may further comprise a polymeric component with which one or more components of the pre-polymeric components may crosslink before or after polymerizing. Any monomer capable of being polymerized to form a biocompatible composition or coating can be used. Monomers may be small molecules, such as acrylic acid or vinyl acetate, or they may be larger molecules (macromers) containing polymerizable groups, such as: acrylate-capped polyethylene glycol (PEG-diacrylate), other polymers containing ethylenically-unsaturated groups, or other polymerizable functional groups. Properties of the monomer, other than polymerizability, will be selected according to the particular biological use, using principles as known in the art. Extensive literature exists on the formulation of polymerizable biocompatible compositions and biocompatible coating materials for particular applications; these formulae can readily be adapted for the pre-polymeric compositions as described herein with little experimentation. In one embodiment the transient colorant is appended to the small molecules or to the monomeric units, or may itself be a monomer or cross-linking agent.

Accordingly, pre-polymeric compositions of the invention may include monomers, macromers or a mixture thereof (and may optionally further comprise one or more additional polymeric components). In one embodiment, the pre-polymeric compositions may be polymerized by using an excitation source such as visible or long wavelength ultraviolet light (lw uv light, 320 nm or greater) to encapsulate or coat either directly or indirectly living tissue with polymeric coatings which conform to the surfaces of cells, tissues or carriers thereof under rapid and mild polymerization conditions. The polymers are formed from such non-toxic pre-polymers, that are preferably water-soluble or substantially water-soluble and preferably too large to diffuse into the cells or tissues whose surfaces are to be coated. Examples of macromers include highly biocompatible PEG hydrogels, which can be rapidly formed in the presence or absence of oxygen, without use of toxic polymerization initiators, at room or physiological temperatures, and at physiological pH.

Any biocompatible monomers may be utilized having at least two polymerizable groups, and in the case of forming biodegradable compositions, the polymerizable groups are separated by at least one degradable region. In one embodiment, when polymerized in water, they form coherent gels which persist until eliminated by self-degradation. Preferred monomers, in addition to being biodegradable, biocompatible, and non-toxic, will also be at least somewhat elastic after polymerization or curing. Elasticity (or simply repeatable stretch ability), is often exhibited by polymers with low modulus. Brittle polymers, including those formed by polymerization of cyanoacrylates, may not be as effective in contact with biological soft tissue.

Any biocompatible macromers may be utilized that contain polymerizable reactive groups, preferably photopolymerizable groups such as acrylate, methacrylate, oligoacrylate, oligomethacrylate groups or other biocompatible polymerizable groups. Such reactive group may include acrylates or diacids that are optionally attached to PEG, PEG derivatives, hyaluronic acid, modified collagen oligomers, and the like. Examples of macromers include PEG-polyacrylate (from a PEG polyol), PEG-cyclodextrin tetra acrylate (PEG grafted a cyclodextrin central ring, and then acrylated), hyaluronic acid methacrylate, formed by grafting PEG to hyaluronic acid and further acrylating; of G include PEG-unsaturated diacid ester formed by esterifying a PEG diol with an unsaturated diacid. Other oligomers or polymers (such as polysaccharides or polypeptides) may be modified in a similar manner.

Polysaccharides include, for example, alginate, hyaluronic acid, chondroitin sulfate, dextran, dextran sulfate, heparin, heparin sulfate, heparin sulfate, chitosan, gellan gum, xanthan gum, guar gum, and K-carrageenan. Polypeptides, for example, include gelatin, collagen, elastin and albumin, whether produced from natural, recombinant or synthetic sources.

Synthetic water-soluble macromers useful in the pre-polymeric compositions can be derived from water-soluble polymers, for example, poly(ethylene oxide) (PEO), poly (ethylene glycol) (PEG), poly(vinyl alcohol) (PVA) poly (vinylpyrrolidone) (PVP), poly(ethyloxazoline) (PEOX) polyaminoacids, pseudopolyamino acids, and polyethyloxazoline, as well as copolymers of these with each other or other water soluble polymers or water insoluble polymers, provided that the conjugate is water soluble. An example of a water-soluble conjugate is a block copolymer of polyethylene glycol and polypropylene oxide, commercially available as a Pluronic™ surfactant.

Polysaccharide macromers can be derived from polysaccharides such as alginate, hyaluronic acid, chondroitin sulfate, dextran, dextran sulfate, heparin, heparin sulfate, heparin sulfate, chitosan, gellan gum, xanthan gum, guar gum, water soluble cellulose derivatives, and carrageenan, which are linked by reaction with hydroxyls or amines on the polysaccharides can also be used to form the macromer solution.

Protein macromers can be derived from materials such as gelatin, collagen, elastin, zein, and albumin, whether produced from natural or recombinant sources. Such proteins can be made free-radical polymerizable by the addition of carbon-carbon double or triple bond-containing moieties, including acrylate, diacrylate, methacrylate, ethacrylate, 2-phenyl acrylate, 2-chloro acrylate, 2-bromo acrylate, itaconate, oligoacrylate, dimethacrylate, oligomethacrylate, acrylamide, methacrylamide, styrene groups, and other biologically acceptable photopolymerizable groups.

In one preferred embodiment, the macromer is formed with a core of a polymer that is water soluble and biocompatible and which has terminal acrylate groups attached. An example of such a core is a polyalkylene oxide polyethylene glycol core and example of the terminal groups are acrylate groups attached by way of hydroxy acid group bridges (such as lactic acid and the like).

The monomers or macromers preferably include cross-linkable groups that are capable of forming covalent bonds with other compounds while in aqueous solution. These cross-linkable groups may permit crosslinking of the macromers to form a gel, either after, or independently from gelation of the macromer. Chemically or ionically crosslinkable groups known in the art may be provided in the monomers or macromers. Preferred crosslinkable groups are unsaturated groups including vinyl groups, allyl groups, cinnamates, acrylates, diacrylates, oligoacrylates, methacrylates, dimethacrylates, oligomethacrylates, or other biologically acceptable polymerizable groups.

Monomers that polymerize by other chemistries that may be used in the pre-polymeric formulations include, for example, monomers that have covalently attached reactive groups that provide the reaction of amines or alcohols with isocyanate or isothiocyanate, or thiols with aldehydes, epoxides, oxiranes, or cyclic imines, amines with aldehydes, epoxides, oxiranes, or cyclic imines are acceptable monomers. Mixtures of covalent polymerization systems may also be utilized. Further, sulfonic acid or carboxylic acid groups may be used for polymerization with monomer that have reactive hydrogen groups.

Useful hydrolysable groups include glycolide, lactide, epsilon-caprolactone, other hydroxy acids, and other useful biologically degradable groups that yield non-toxic or normal metabolites in the body may also be utilized. Preferred are pre-polymeric formulations that produce poly(alpha-hydroxy acids) are poly(glycolic acid), poly(DL-lactic acid) and poly(L-lactic acid). Other useful materials include pre-polymeric materials that produce poly(amino acids), polycarbonates, poly(anhydrides), poly(orthoesters), poly(phosphazines) and poly(phosphoesters). Materials that produce polylactones such as poly(epsilon-caprolactone), poly(delta-caprolactone), poly(delta-valerolactone) and poly(gamma-butyrolactone), for example, are also useful. The pre-polymeric compositions may produce biodegradable regions that have a degree of polymerization ranging from one up to values that would yield a product that was not substantially water-soluble. Thus, monomeric, dimeric, trimeric, oligomeric, and polymeric hydrolysable regions may be provided by the pre-polymeric compositions.

Biodegradable regions can be provided by linkages susceptible to biodegradation, such as ester, peptide, anhydride, orthoester, phosphazine and phosphoester bonds. The time required for a polymer (or gel) to degrade can be tailored by selecting appropriate monomers. Differences in crystallinity can also be exploited to alter degradation rates. For relatively crystalline or hydrophobic polymers, actual mass loss may only begin when the oligomeric fragments are small enough to be water-soluble. Thus, the initial molecular weight and structure of the polymer produced can be varied to influence the degradation rate.

A. Polymerization Methods

In one embodiment, the pre-polymeric composition may be polymerized by using a photosensitive non-toxic dye as an initiator in addition to the excitation source, where the dye does not substantially diffuse into cells or tissues, such as methylene blue or eosin Y. In such a case, the pre-polymer may be photopolymerized with visible or with low wavelength ultraviolet light. Other dyes that diffuse into the cells but are nontoxic, such as ethyl eosin, may also be used with the excitation source. Pre-polymerization can be conducted in a non-cytotoxic manner to avoid excessive light being absorbed by cells by use of a proper chromophore. A preferred light source is used where cells are largely transparent to the light, as opposed to very short wavelength UV radiation, which can be strongly absorbed by cellular proteins and nucleic acids and can be cytotoxic. Preferably, low levels of irradiation (5-500 mW) are usually enough to induce polymerization in a time period of between milliseconds to a few seconds for most macromers. A second reason for the lack of cytotoxicity is that the polymerizable species does not diffuse into cells.

Resulting polymers can act as semipermeable membranes, as adhesives as tissue supports, as plugs, as barriers to prevent the interaction of one cell tissue with another cell or tissue, and as carriers for bioactive species. A wide variety of surfaces, with different geometries, can be coated with a three dimensionally cross-linked network of such polymeric materials. The polymers can be formed into a matrix for delivery of biologically active materials, including proteins, polysaccharides, small molecule therapeutic compounds with drug activity, and nucleic acids.

In one preferred embodiment, the resulting polymer is used to form a layer on the inside of the lumen of a blood vessel, either for structural support, prevention of thrombosis and inflammatory reactions at the lumen surface, and/or delivery of therapeutic agents to the blood vessel. In another preferred embodiment, the resulting polymer is used to create a semipermeable barrier around cells such as islets of Langerhans to protect the cell by preventing the passage of immunoglobulins molecules or cells, while allowing free transfer of nutrients, gases and small cell products. Such treated islets may be useful in treating diseases that result from deficiencies in metabolic processing, or diseases like diabetes which arise from insufficient concentrations of bioregulator molecules.

V. Crosslinkable Polymeric or Pre-Polymeric Compositions

In accordance with one embodiment of the present invention, the formulation is a crosslinkable polymer composition is provided that contains a minimum of three components, each of which participates in a reaction that results in a crosslinked matrix, where the transient colorant may be attached to one of the crosslinkable components or may be in a mixture with the crosslinkable components. The crosslinkable components of the composition are selected so that crosslinking gives rise to a biocompatible, non-immunogenic matrix useful in a variety of contexts, including adhesion, biologically active agent delivery, tissue augmentation, and other applications.

A. Starting Materials

Examples of starting materials suitable for crosslinking and compositions thereof are described in commonly owned published patent applications US20020042473A1 to Trollsas et al. and US20010003126A1 to Rhee et al., which are incorporated herein by reference. Other examples are provided above in the description of the polymeric and pre-polymeric compositions, including cross-reference published patent documents.

B. Crosslinking the Crosslinkable Compositions

Any number of crosslinking techniques may be used to effect crosslinking of the aforementioned compositions. Generally, however, the components are selected such that crosslinking occurs fairly rapidly upon admixture of all components of the crosslinkable composition with an aqueous medium optionally in the presence of an adequate excitation agent.

For crosslinking compositions in which one or more components contain hydroxyl and/or thiol groups as nucleophilic moieties, the aqueous medium with which the crosslinking composition (or components thereof) are admixed should contain a basic reagent that is effective to increase the nucleophilic reactivity of the hydroxyl and/or thiol group (and thus the rate of the nucleophile-electrophile reactions) but that is preferably non-nucleophilic so as to avoid reaction with any electrophilic groups present. A catalytic amount of base can be used, and/or a base-containing buffer. In an alternative but less preferred embodiment, a reactive base can be used that participates as a reactant in the crosslinking reaction.

In general, the combined concentration of all crosslinkable components in the aqueous admixture will be in the range of about 1 to 50 wt. %, generally about 2 to 40 wt. %. However, a preferred concentration of the crosslinkable composition in the aqueous medium—as well as the preferred concentration of each crosslinkable component therein—will depend on a number of factors, including the type of component, its molecular weight, and the end use of the composition. For example, use of higher concentrations of the crosslinkable components, or using highly functionalized components, will result in the formation of a more tightly crosslinked network, producing a stiffer, more robust gel. As such, compositions intended for use in tissue augmentation will generally employ concentrations of crosslinkable components that fall toward the higher end of the preferred concentration range. Compositions intended for use as bioadhesives or in adhesion prevention do not need to be as firm and may therefore contain lower concentrations of the crosslinkable components. The appropriate concentration of each crosslinkable component can easily be optimized to achieve a desired gelation time and gel strength using routine experimentation.

VI. Administration and Use

The compositions of the present invention may be administered before, during or after polymerization and/or crosslinking. Certain uses, which are discussed in greater detail below, such as tissue augmentation, may require the compositions to be crosslinked before administration, whereas other applications, such as tissue adhesion, require the compositions to be administered before crosslinking has reached "equilibrium." The point at which polymerization and optional crosslinking has reached equilibrium may be defined as the point at which the composition no longer feels tacky or sticky to the touch.

As described above, use of these compositions has distinct advantages over traditional compositions that do not incorporate a transient. The initial application and placement of the compositions can be verified by excitation of the transient colorant, which can significantly contribute to the efficiency of using such compositions in conjunction with surgical procedures.

The compositions of the present invention are generally delivered to the site of administration in such a way that the individual components of the composition come into contact with one another for the first time at the site of administration, or immediately preceding administration. Thus, the compositions of the present invention are preferably delivered to the site of administration using an apparatus that allows the components to be delivered separately. Such delivery systems usually involve a multi-compartment spray device. Alternatively, the components can be delivered separately using any type of controllable extrusion system, or they can be delivered manually in the form of separate pastes, liquids or dry powders, and mixed together manually at the site of administration. Many devices that are adapted for delivery of multi-component tissue sealants/hemostatic agents are well known in the art and can also be used in the practice of the present invention.

Yet another way of delivering the compositions of the present invention is to prepare the reactive components in inactive form as either a liquid or powder. Such compositions can then be activated after application to the tissue site, or immediately beforehand, by applying an activator. In one embodiment, the activator is a buffer solution having a pH that will activate the composition once mixed therewith. Still another way of delivering the compositions is to prepare preformed sheets, and apply the sheets as such to the site of administration.

Yet another way of delivering the compositions of the present invention is to prepare the reactive components in inactive form as either a liquid or powder. Such compositions can then be activated after application to the tissue site, or immediately beforehand, by applying an activator. In one embodiment, the activator is a buffer solution having a pH that will activate the composition once mixed therewith. Still another way of delivering the compositions is to prepare preformed sheets, and apply the sheets as such to the site of administration.

The compositions of the present invention can be used in a variety of different applications, and components may be cross-linked where desired for a particular application of the compositions. In general, the present compositions can be adapted for use in any tissue engineering application. Particularly useful applications are where synthetic gel matrices are currently being utilized, and cross-linked compositions are preferred for such applications. For example, the compositions of the present invention are useful as tissue sealants, in tissue augmentation, in tissue repair, as hemostatic agents, in preventing tissue adhesions, in providing surface modifications, and in drug/cell/gene delivery applications. One of skill in the art can easily determine the appropriate administration protocol to use with any particular composition having a known gel strength and gelation time. A more detailed description of several specific applications is given below:

In one implementation, the compositions may be utilized as "solid implants" which solid objects are designed for insertion and use within the body. This includes bone and cartilage implants (e.g., artificial joints, retaining pins, cranial plates, and the like, of metal, plastic and/or other materials), breast implants (e.g., silicone gel envelopes, foam forms, and the like), catheters and cannulas intended for long-term use (beyond about three days) in place, artificial organs and vessels (e.g., artificial hearts, pancreases, kidneys, blood vessels, and the like), drug delivery devices (including monolithic implants, pumps and controlled release devices such as ALZET® minipumps, steroid pellets for anabolic growth or contraception, and the like), sutures for dermal or internal use, periodontal membranes, ophthalmic shields, corneal lenticules, and the like.

The compositions may be utilized with "suitable fibrous materials" to provide improved surgical implements. Such implements can use a fibrous material which is substantially insoluble in water, non-immunogenic, biocompatible, and immiscible with the compositions of the invention. The fibrous material may comprise any of a variety of materials having these characteristics and may be combined with compositions herein in order to form and/or provide structural integrity to various implants or devices used in connection with medical and pharmaceutical uses. For example, cross-linkable compositions of the invention can be coated on a "suitable fibrous material," which can then be wrapped around a bone to provide structural integrity to the bone. Thus, the "suitable fibrous material" is useful in forming the "solid implants" of the invention.

Other uses for the present compositions will be apparent to one of ordinary skill in this field. Below are some biological uses that may incorporate compositions according to the invention.

Tissue Sealants and Adhesives: In a preferred application, the compositions described herein can be used for medical conditions that require a coating or sealing layer to prevent the leakage of gases, liquid or solids. The method entails applying both components to the damaged tissue or organ to seal 1) vascular and or other tissues or organs to stop or minimize the flow of blood; 2) thoracic tissue to stop or minimize the leakage of air; 3) gastrointestinal tract or pancreatic tissue to stop or minimize the leakage of fecal or tissue contents; 4) bladder or ureters to stop or minimize the leakage of urine; 5) dura to stop or minimize the leakage of CSF; and 6) skin or serosal tissue to stop the leakage of serosal fluid. These compositions may also be used to adhere tissues together such as small vessels, nerves or dermal tissue. The material can be used 1) by applying it to the surface of one tissue and then a second tissue may be rapidly pressed against the first tissue or 2) by bringing the tissues in close juxtaposition and then applying the material. In addition, the compositions can be used to fill spaces in soft and hard tissues that are created by disease or surgery. Integrity of the coating or sealing can be verified by excitation and observation of the transient colorant included within the coating or sealant composition.

Therapeutic Scar Tissue Promotion: The compositions of the invention may also be used as, or to augment, compositions for the promotion or generation of localized therapeutic scar tissue formation. For example, an implant, stint, or other type of aneurysm treatment might function in a more desirable way if it were formed of or coated with a composition according to the invention that is selected to lead to the promotion of therapeutic scar tissue formation. The transient colorant may be exited to check for placement or integrity of the composition according to the invention.

In a preferred method of use, a composition of the present invention is used in conjunction with an aneurysm treatment method to enhance the efficacy and safety of these methods. Thus, an embolic mass such as an occlusion coil is introduced into an aneurysm to induce clot formation, following or prior to which a composition of the present invention is deployed as a sealant or glue to ensure that neither the occluding element nor any clots migrate out of the aneurysm and out into the vasculature. This approach is particularly beneficial in wide necked aneurysms where embolic agents have until now been difficult or impossible to keep in. Alternatively, an embolic agent may be introduced into the aneurysm to substantially fill the aneurysmal cavity, following or prior to which the device of the present invention may be deployed across the entrance of the aneurysm to ensure that the embolic agent does not migrate into the vasculature of the patient. In a preferred aspect, the composition is selected to incorporate a medicine that is slowly released into the aneurysm following deployment of the device, or otherwise to enhance or prevent clot formation, cell growth, scar tissue formation, and other desirable or undesirable effects.

In another aspect, the composition of the present invention can be used to treat a substantially hollow space or volume in a patient's body having fluid flowing within (such as, for example, a body cavity such as an aneurysm, or a body lumen such as a fistula or a vein) by reducing at least partially the peak fluid flow and peak fluid pressure experienced by the cavity or lumen. Therefore, in an alternative aspect the present invention provides a composition that can act as a diverter for diverting at least partially the arterial blood flow away from the entrance of a body cavity or lumen, and as an anchoring element for securing the diverter at a particular intravascular location and, for certain embodiments, in a particular angular orientation with respect to the entrance of the cavity or lumen. For example, the diverter may operate to divert all or a portion of the arterial blood flow away from the neck of an aneurysm, or to completely block all such blood flow into the aneurysm, to the net effect of reducing the peak blood pressure experienced by the aneurysm. The diverter may be comprised of one or more coils, ribbons in parallel or intertwined configurations, flexible membranes, foam pads, and other elements formed with protrusions or surfaces for biasing the arterial blood flow in a particular direction. In a preferred aspect the composition is selected to promote therapeutic scar tissue formation near the diverter.

In another embodiment, the composition is selected to promote or generate therapeutic scar tissue of fascial tissue origin. The composition may be applied along with laser energy, focused ultrasound energy, microwave energy, a caustic composition, a pleurodesis agent, a sclerosing agent, or a growth factor that will enhance therapeutic scar tissue formation or generation. The facial tissue may be a member selected from the group: anterior sacro-coccygeal ligament; arcus tendineus fasciae pelvis; fasciae of the obturator interuus muscle; the arcs tendineus levator ani; bulb-ocavenosus muscle; ischiocavenosus muscle; urethrovaginal sphincter; m. compressor urethrae muscle; m. sphincter urethrovaginal muscle; structures of the bladder and urethra; urethrovesical fascia; detrusor muscle; pubo-coccygeus muscle; structures of the vagina; vagino-uterine fascia; lamina propria; pubo-urethral or puboprostatic ligaments; pubo-vesicle ligament and posterior pubo-urethral or pubo-prostatic ligament; pubovesicle muscle; pubocervical fascia; structures of the uterus; round ligament; sacrouterine ligament; and broad ligament; structures off the bowel; rectal fascia and Mackenrodt's ligament, or the like In one preferred embodiment a cell, tissue or other implant is coated with the composition according to the invention in order to promote or generate therapeutic scar tissue of facial origin. Particularly preferred is therapeutic tissue promotion with respect to the urinary tract, digestive tract, or vascular system, including tissue on or near the bladder valve, urethral tissue, sphincter tissue, or tissue that is located on or near vascular valves.

Biologically Active Agent Delivery: The compositions of the invention may also be used as therapeutic compositions for localized delivery of various drugs and other biologically active agents. For example, biologically active agents such as growth factors may be delivered from the composition to a local tissue site in order to facilitate tissue healing and regeneration.

The placement of therapeutic compositions that contain biologically active agents can be verified by excitation and observation of the transient colorant of the composition. Also, the condition of previously placed and existing therapeutic compositions can be verified by excitation and observation of the transient colorant.

The term "biologically active agent" of the therapeutic compositions refers to an organic molecule that exerts biological effects in vivo. Examples of biologically active agents include, without limitation, enzymes, receptor antagonists or agonists, hormones, growth factors, autogenous bone marrow, antibiotics, antimicrobial agents and antibodies. The term "biologically active agent" is also intended to encompass various cell types and genes that can be incorporated into the compositions of the invention.

Preferred biologically active agents for use in the compositions of the present invention are cytokines, which is used to describe biologically active molecules including growth factors and active peptides, which aid in healing or re-growth of normal tissue. The function of cytokines is two-fold: 1) they can incite local cells to produce new collagen or tissue, or 2) they can attract cells to the site in need of correction. As such, cytokines serve to encourage "biological anchoring" of a biocompatible implant within the host tissue. Cytokines can either be admixed with the polymer or chemically coupled to the polymer. For example, one may incorporate cytokines such as epidermal growth factor (EGF), transforming growth factor (TGF)-α, TGF-β (including any combination of TGF-βs), TGF-β1, TGF-β2, platelet derived growth factor (PDGF-AA, PDGF-AB, PDGF-BB), acidic fibroblast growth factor (FGF), basic FGF, connective tissue activating peptides (CTAP), β-thromboglobulin, insulin-like growth factors, tumor necrosis factors (TNF), interleukins, colony stimulating factors (CSFs), erythropoietin (EPO), nerve growth factor (NGF), interferons (IFN) bone morphogenic protein (BMP), osteogenic factors, and the like. Incorporation of cytokines, and appropriate combinations of cytokines can facilitate the re-growth and remodeling of the implant into normal bone tissue, or may be used in the treatment of wounds. Members of the transforming growth factor (TGF) supergene family, which are multifunctional regulatory proteins, are particularly preferred. Members of the TGF supergene family include the beta transforming growth factors (for example, TGF-.beta.1, TGF-.beta.2, TGF-.beta.3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Biologically active agents may be incorporated into the polymer composition by admixture (before or after crosslinking), or may be incorporated into the pre-polymeric composition prior to polymerization and/or crosslinking. In another alternative, the agents may be incorporated into the composition by binding these agent to functional groups on the synthetic polymers or pre-polymers before forming a crosslinked polymer matrix or after the matrix is formed. Processes for covalently binding biologically active agents such as growth factors using functionally activated polyethylene glycols are described in commonly assigned U.S. Pat. No. 5,162,430, issued Nov. 10, 1992, to Rhee et al. Such compositions preferably include linkages that can be easily biodegraded, for example as a result of enzymatic degradation, resulting in the release of the active agent into the target tissue, where it will exert its desired therapeutic effect.

A simple method for incorporating biologically active agents containing nucleophilic groups into a polymer composition involves mixing the active agent with a polyelectrophilic component prior to addition of the polynucleophilic component.

By varying the relative molar amounts of the different components of the composition, it is possible to alter the net charge of the resulting composition, in order to prepare a composition, optionally a crosslinked matrix, for the delivery of a charged compound such as a protein or ionizable drug. As such, the delivery of charged proteins or drugs, which would normally diffuse rapidly out of a neutral carrier matrix, can be controlled.

For example, if a molar excess of a polynucleophilic component is used, the resulting matrix has a net positive charge and can be used to ionically bind and deliver negatively charged compounds. Examples of negatively charged compounds that can be delivered from these matrices include various drugs, cells, proteins, and polysaccharides. Negatively charged collagens, such as succinylated collagen, and glycosaminoglycan derivatives such as sodium hyaluronate, keratan sulfate, keratosulfate, sodium chondroitin sulfate A, sodium dermatan sulfate B, sodium chondroitin sulfate C, heparin, esterified chondroitin sulfate C, and esterified heparin, can be effectively incorporated into the crosslinked polymer matrix as described above.

If a molar excess of a polyelectrophilic component is used, the resulting matrix has a net negative charge and can be used to ionically bind and deliver positively charged compounds. Examples of positively charged compounds that can be delivered from these matrices include various drugs, cells, proteins, and polysaccharides. Positively charged collagens, such as methylated collagen, and glycosaminoglycan derivatives such as esterified deacetylated hyaluronic acid, esterified deacetylated desulfated chondroitin sulfate A, esterified deacetylated desulfated chondroitin sulfate C, deacetylated desulfated keratan sulfate, deacetylated desulfated keratosulfate, esterified desulfated heparin, and chitosan, can be effectively incorporated into the crosslinked polymer matrix as described above.

Delivery of cells and genes: The polymer or pre-polymeric compositions of the present invention can also be used to deliver various types of living cells or genes to a desired site of administration in order to form new tissue. The term "genes" as used herein is intended to encompass genetic material from natural sources, synthetic nucleic acids, DNA, antisense-DNA and RNA.

Placement of compositions used for delivery of cells and/or genes can be verified by verified excitation and observation of the transient colorant of the composition. Also, the condition of previously placed and existing delivery compositions can be verified by excitation and observation of the transient colorant.

When used to deliver cells, for example, mesenchymal stem cells can be delivered to produce cells of the same type as the tissue into which they are delivered. Mesenchymal stem cells are not differentiated and therefore can differentiate to form various types of new cells due to the presence of an active agent or the effects (chemical, physical, etc.) of the local tissue environment. Examples of mesenchymal stem cells include osteoblasts, chondrocytes, and fibroblasts. Osteoblasts can be delivered to the site of a bone defect to produce new bone; chondrocytes can be delivered to the site of a cartilage defect to produce new cartilage; fibroblasts can be delivered to produce collagen wherever new connective tissue is needed; neurectodermal cells can be delivered to form new nerve tissue; epithelial cells can be delivered to form new epithelial tissues, such as liver, pancreas, etc.

The cells or genes may be either allogeneic or xenogeneic in origin. For example, the compositions can be used to deliver cells or genes from other species that have been genetically modified. Because the compositions of the invention are not easily degraded in vivo, cells and genes entrapped within the crosslinked polymer compositions will be isolated from the patient's own cells and, as such, will not provoke an immune response in the patient. In order to entrap the cells or genes within a crosslinked polymer matrix, the cells or genes are pre-mixed with the polynucleophilic component(s), and then the polyelectrophilic component(s) are added to the mixture to form a crosslinked matrix, thereby entrapping the cells or genes within the matrix. Alternatively, the initial pre-mixing may be carried out with the polyclectrophilic component(s), followed by subsequent addition of the polynucleophilic component(s).

As discussed above for biologically active agents, when used to deliver cells or genes, the synthetic polymers preferably also contain biodegradable groups to aid in controlled release of the cells or genes at the intended site of delivery.

Bioadhesives: As used herein, the terms "bioadhesive", "biological adhesive", and "surgical adhesive" are used interchangeably to refer to biocompatible compositions capable of effecting temporary or permanent attachment between the surfaces of two native tissues, or between a native tissue surface and either a non-native tissue surface or a surface of a synthetic implant.

The placement and integrity of bioadhesives containing the compositions according to the invention can be verified by excitation and observation of the transient colorant of the composition. Also, the condition of previously placed and existing adhesive compositions can be verified by excitation and observation of the transient colorant of the compositions.

A general method for effecting the attachment of a first surface to a second surface using bioadhesives is where the composition is applied to a first surface, and the first surface is then contacted with a second surface to effect adhesion therebetween. Preferably, all reactive components of the composition are first mixed to initiate crosslinking, and then delivered to the first surface before substantial crosslinking has occurred. The first surface is then contacted with the second surface, preferably immediately, to effect adhesion. At least one of the first and second surfaces is preferably a native tissue surface.

The two surfaces may be held together manually, or using other appropriate means, while the crosslinking reaction is proceeding to completion. Crosslinking is typically sufficiently complete for adhesion to occur within about 5 to 60 minutes after mixing of the first and second synthetic polymers. However, the time required for complete crosslinking to occur is dependent on a number of factors, including the type and molecular weight of each reactive component, the degree of functionalization, and the concentration of the crosslinkable composition (i.e., higher concentrations result in faster crosslinking times).

At least one of the first and second surfaces is preferably a native tissue surface. As used herein, the term "native tissue" refers to biological tissues that are native to the body of the patient being treated. As used herein, the term "native tissue" is intended to include biological tissues that have been elevated or removed from one part of the body of a patient for implantation to another part of the body of the same patient (such as bone autografts, skin flap autografts, etc.). For example, the compositions of the invention can be used to adhere a piece of skin from one part of a patient's body to another part of the body, as in the case of a burn victim.

The other surface may be a native tissue surface, a non-native tissue surface, or a surface of a synthetic implant. As used herein, the term "non-native tissue" refers to biological tissues that have been removed from the body of a donor patient (who may be of the same species or of a different species than the recipient patient) for implantation into the body of a recipient patient (e.g., tissue and organ transplants). For example, the crosslinkable polymer compositions of the present invention can be used to adhere a donor cornea to the eye of a recipient patient.

As used herein, the term "synthetic implant" refers to any biocompatible material intended for implantation into the body of a patient not encompassed by the above definitions for native tissue and non-native tissue. Synthetic implants include, for example, artificial blood vessels, heart valves, artificial organs, bone prostheses, implantable lenticules, vascular grafts, stents, and stent/graft combinations, etc.

Ophthalmic Applications: Compositions according to the invention may be selected for optical clarity, which is particularly well suited for use in ophthalmic applications (a transient colorant may be utilized for locating placement of the implant, or may be used to provide protection of the eye against ultraviolet light). For example, a synthetic lenticule for correction of vision can be attached to the Bowman's layer of the cornea of a patient's eye using the methods of the present invention. As disclosed in U.S. Pat. No. 5,565,519 to Rhee et al., a chemically modified collagen (such as succinylated or methylated collagen) that is in substantially nonfibrillar form at pH 7 can be crosslinked using a synthetic hydrophilic polymer, then molded into a desired lenticular shape and allowed to complete crosslinking. The resulting crosslinked collagen lenticule can then be attached to the Bowman's layer of a de-epithelialized cornea of a patient's eye using the methods of the present invention. By applying the reaction mixture comprising the first and second synthetic polymers to the anterior surface of the cornea, then contacting the anterior surface of the cornea with the posterior surface of the lenticule before substantial crosslinking has occurred, electrophilic groups on the second synthetic polymer will also covalently bind to collagen molecules in both the corneal tissue and the lenticule to firmly anchor the lenticule in place. Alternatively, the reaction mixture can be applied first to the posterior surface of the lenticule, which is then contacted with the anterior surface of the cornea.

The compositions of the present invention are also suitable for use in vitreous replacement.

Tissue Augmentation: The compositions of the invention can also be used for augmentation of soft or hard tissue within the body of a mammalian subject. Placement of the augmentation composition can be verified by excitation and observation of the transient colorant of the composition. As such, they may be better than currently marketed collagen-based materials for soft tissue augmentation, because they are less immunogenic and more persistent. Examples of soft tissue augmentation applications include sphincter (e.g., urinary, anal, esophageal) augmentation and the treatment of rhytids and scars. Examples of hard tissue augmentation applications include the repair and/or replacement of bone and/or cartilaginous tissue.

The compositions of the invention are particularly suited for use as a replacement material for synovial fluid in osteoarthritic joints, serving to reduce joint pain and improve joint function by restoring a soft hydrogel network in the joint. The crosslinked compositions can also be used as a replacement material for the nucleus pulposus of a damaged intervertebral disk. The nucleus pulposus of the damaged disk is first removed, and the crosslinkable composition is then injected or otherwise introduced into the center of the disk. The composition may either be crosslinked prior to introduction into the disk, or allowed to crosslink in situ.

In a general method for effecting augmentation of tissue within the body of a mammalian subject, the reactive components of the crosslinkable composition are injected simultaneously to a tissue site in need of augmentation through a small-gauge (e.g., 25-32 gauge) needle. Once inside the patient's body, the nucleophilic groups on the polynucleophilic component(s) and the electrophilic groups on the polyelectrophilic component(s) react with each other to form a crosslinked polymer network in situ. Electrophilic groups on the polyelectrophilic component(s) may also react with primary amino groups on lysine residues of collagen molecules within the patient's own tissue, providing for "biological anchoring" of the compositions with the host tissue.

Adhesion Prevention: Another use of the compositions of the invention is to coat tissues in order to prevent the formation of adhesions following surgery or injury to internal tissues or organs. Preferred compositions for adhesion prevention are cross-linkable compositions according to the invention.

The placement of adhesion prevention compositions can be verified by excitation and observation of the transient colorant of the composition. Also, the condition of previously placed adhesion prevention compositions can be verified by excitation and observation of the transient colorant.

In a general method for coating tissues to prevent the formation of adhesions following surgery, the reactive components are mixed and a thin layer of the reaction mixture is then applied to the tissues comprising, surrounding, and/or adjacent to the surgical site before substantial crosslinking has occurred. Application of the reaction mixture to the tissue site may be by extrusion, brushing, spraying (as described above), or by any other convenient means.

Following application of the reaction mixture to the surgical site, crosslinking is allowed to continue in situ prior to closure of the surgical incision. Once crosslinking has reached equilibrium, tissues that are brought into contact with the coated tissues will not adhere thereto. The surgical site can then be closed using conventional means (sutures, etc.).

In general, compositions that achieve complete crosslinking within a relatively short period of time (i.e., 5-15 minutes following admixture of the reactive components) are preferred for use in the prevention of surgical adhesions, so that the surgical site may be closed relatively soon after completion of the surgical procedure.

Coating Material for Synthetic Implants: Another use of the polymer compositions of the invention is as a coating material for synthetic implants. Such synthetic implants can be made of a wide variety of materials, including composites and laminated materials.

The placement or location of synthetic implants can be verified by excitation and observation of the transient colorant of the coating composition. Also, the condition of previously placed and existing synthetic implants can be verified by excitation and observation of the transient colorant of the coating composition.

In a general method for coating a surface of a synthetic implant, the reactive components of the crosslinkable composition are mixed with an aqueous medium, and a thin layer of the reaction mixture is then applied to a surface of the implant before substantial crosslinking has occurred. In order to minimize cellular and fibrous reaction to the coated implant, the reaction mixture is preferably prepared to have a net neutral charge. Application of the reaction mixture to the implant surface may be by extrusion, brushing, spraying (as described above), or by any other convenient means. Following application of the reaction mixture to the implant surface, crosslinking is allowed to continue until complete crosslinking has been achieved.

Although this method can be used to coat the surface of any type of synthetic implant, it is particularly useful for implants where reduced thrombogenicity is an important consideration, such as artificial blood vessels and heart valves, vascular grafts, vascular stents, and stent/graft combinations. The method may also be used to coat implantable surgical membranes (e.g., monofilament polypropylene) or meshes (e.g., for use in hernia repair). Breast implants may also be coated using the above method in order to minimize capsular contracture.

The compositions of the present invention may also be used to coat lenticules, which are made from either naturally occurring or synthetic polymers.

Treatment of Aneurysm: The compositions of the invention can be extruded or molded in the shape of a string or coil, then dehydrated. The resulting dehydrated string or coil can be delivered via catheter to the site of a vascular malformation, such as an aneurysm, for the purpose of vascular occlusion and, ultimately, repair of the malformation. The dehydrated string or coil can be delivered in a compact size and will rehydrate inside a blood vessel, swelling several times in size compared to its dehydrated state, while maintaining its original shape.

The placement of the string or coil comprising the compositions according to the invention can be verified by excitation and observation of the transient colorant of the composition. Also, the condition of previously placed and existing strings or coils comprising the compositions can be verified by excitation and observation of the transient colorant of the composition.

Other Uses: As discussed in U.S. Pat. No. 5,752,974 to Rhee et al., compositions can be used to block or fill various lumens and voids in the body of a mammalian subject. Particularly preferred for such applications are cross-linkable compositions. The filling of the various lumens and voids with such compositions can be verified by excitation and observation of the transient colorant of the compositions that are used to fill the lumens and voids. Such may be used for preventative, diagnostic or other therapeutic purposes. The compositions can also be used as biosealants to seal fissures or crevices within a tissue or structure (such as a vessel), or junctures between adjacent tissues or structures, to prevent leakage of blood or other biological fluids. The presence and condition of such biosealants can be observed by excitation of the transient colorant of the compositions.

The compositions can also be used as a large space-filling device for organ displacement in a body cavity during surgical or radiation procedures, for example, to protect the intestines during a planned course of radiation to the pelvis. Coverage and displacement may be observed by excitation of the transient colorant of the compositions.

The compositions of the invention can also be coated onto the interior surface of a physiological lumen, such as a blood vessel or Fallopian tube, thereby serving as a sealant to prevent restenosis of the lumen following medical treatment, such as, for example, balloon catheterization to remove arterial plaque deposits from the interior surface of a blood vessel, or removal of scar tissue or endometrial tissue from the interior of a Fallopian tube. A thin layer of the reaction mixture is preferably applied to the interior surface of the vessel (for example, via catheter) immediately following mixing of the first and second synthetic polymers. Placement of the thin layer is verified by excitation and observation of the transient colorant. Because compositions of the invention can be provided which are not readily degradable in vivo, the potential for restenosis due to degradation of the coating can be minimized. Crosslinked polymer compositions having a net neutral charge can be utilized to further minimize the potential for restenosis.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains. All patents, patent applications, patent publications, journal articles and other references cited herein are incorporated by reference in their entireties.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

Experimental:

General Procedures. Transient colorants were subjected to irradiation or other sterilization methods to determine if they would be stable. Standard chemical mixing, measuring, and analytical methods were utilized. Solubilities for effective amounts of transient colorants mixed in starting materials (and in the final compositions) were verified by routine mixing followed by analytical procedures.

Materials. Unless otherwise stated, all other chemicals were purchased or manufactured from the Aldrich, Sigma, Strem, or Nova Biochem Chemical Companies, or equivalent sources and were used as delivered. The term "COH102" in the examples below refers to a composition made by mixing powdered pentaerythritol polyethylene glycol ether tetrasuccinimidyl glutarate and a 0.5 mM sodium phosphate buffer with a pH of 6. The term "COH206" in the examples below refers to a composition made by mixing powdered pentaerythritol polyethylene glycol ether tetrathiol and a 117 mM monobasic sodium phosphate, 183 mM sodium carbonate buffer with a pH of 9.6. The term "C0H204" in the examples below refers to a composition made by mixing powdered penta-erythritol polyethylene glycol ether tetra amino and a 117 mM monobasic sodium phosphate, 183 mM sodium carbonate buffer with a pH of 9.6. The term COSEAL® (Angiotech Pharmaceuticals (US) Inc., North Bend, Wash.) in the examples refers to a reaction product of COH102 and COH206 that may incorporate other recited ingredients. If necessary, materials are sterilized by radiation or other acceptable biological methods.

Fluorescein in COSEAL®

Fluorescein was tested at 0.1% in COH102 and COH206 buffer and found to be soluble. To test in COSEAL®, one-fifth volume of COH102 buffer was replaced with 0.1% to 1.0% fluorescein in COH102 buffer, and the PEGs, COH102, and COH206 were added and dissolved. The fluorescence was noted to go away upon dissolving the mixed PEGs, and the color changed to a light yellow. However, when the solution was sprayed with COH206 buffer to make the reaction product COSEAL®, the fluorescence returned. The final fluorescein concentration was 0.01% to 0.1% by weight of the final composition.

The fluorescence of COSEAL® containing fluorescein as the transient colorant was yellow with a slight green tint under standard room fluorescent lighting. A similar fluorescence was seen when the COSEAL® was illuminated with a standard light used in laproscopic surgery (Circon 300 W xenon). Long wave uv light generated a bright yellow-green fluorescence. Short wave uv did not generate much color or fluorescence. The FocalSeal xenon light and a Demetron light (by Optilux) gave a bright yellow color.

Other Transient Colorants In COSEAL®

Other transient colorants according to the invention were evaluated as described in Example 1 and subjected to the same or a different excitation source to observe the transient colorant. The concentration of the transient colorant was generally between 0.01 wt. % to 0.1 wt. % in the final composition.

EXAMPLE 3

COSEAL® with Fluorescein as a Tissue Coating or Sealant

COSEAL®, with fluorescein added at a final concentration of 0.01% and 0.1% was sprayed, with air assist, on skinless chicken and liver. Fluorescence was visible under standard room fluorescent lighting as well as a Circon xenon light, used for laproscopic surgery. The higher concentration showed a more intense fluorescence. Fluorescein at a final concentration of 0.05% was mixed with an equal concentration of D & C Green 5 dye (Spectrum lot PA0628) and again sprayed, with air assist, on skinless chicken and liver. Fluorescence was visible under standard room fluorescent lighting as well as the Circon xenon light. Photographs were taken of the COSEAL®-covered meat where the transient colorant was in an excited state.

EXAMPLE 4

Elution of Fluorescein from COSEAL® in a Solvent

COSEAL®, with fluorescein added at a final concentration of 0.1%, was sprayed, with air assist, on sausage casing. The sausage casing was immersed in excess PBS with gentle stirring and the fluorescein was allowed to elute as a function of time. Ninety percent eluted in approximately 30 minutes at room temperature. The thickness of the film was calculated to be 0.05 mm.

EXAMPLE 5

Tensile Strength Evaluation of Compositions with Fluorescein

Materials and Methods: Penta-erythritol polyethylene glycol ether tetrathiol, MW=10,000 (for COH206); penta-erythritol polyethylene glycol ether tetrasuccinimidyl-glutarate, MW=10,000 (for COH102); and penta-erythritol polyethylene glycol ether tetra amino, MW=10,000 (for COH204), were purchased from Shearwater Polymers, Inc. (Huntsville, Ala.). Cyanoacrylate was purchased over the counter. Gelatin, 70-100 Bloom and fluorescein were purchased from Sigma (Saint Louis, Mo.). Sulfoethylene glycol bis succinimidyl succinate (S-EGS); dimethyl suberimidate (DMS); and disuccinimidyl glutarate (DSG) were purchased from Pierce Chemical Company, Rockford, Ill. Polyethylene glycol diacrylate (PEG-DA), MW=1,000; polyethylene glycol dimethacrylate (PEG-DM); and 2-hydroxy-ethyl methacrylate (HEMA) were purchased from Polysciences, Inc., Warrington, Pa. Polypropyleneoxide diacrylate (PPO-DA), MW=600; polypropyleneoxide bis-2-aminopropyl ether (PPO-BA), MW=230 and 2,000 mol; polytetrahydrofuran bis-3-aminopropyl ether (PTHF-BA), MW=350 and 1,100; pentaerythritol tetrakis(3-mercapto propionate) (PE-4SHP), pentaerythritol triacryalte, (PE-3A), and potassium metabisulfite were purchased from Aldrich Chemical Company, Milwaukee, Wis. Ammonium persulfate was purchased from Biorad, Inc., Richmond Calif. Methylated collagen was prepared from purified bovine corium collagen, following a method modified from U.S. Pat. No. 4,164,559 (see Example 11). Gel preparation was as set forth below except that one fifth volume of the buffer for COH102 or COH206 were replaced with from 0.1% to 1.0% fluorescein in that buffer.

Gel Preparation:

a. COH102/COH206: 100 mg COH102 were dissolved in 0.5 mM sodium phosphate buffer (pH 6.0) (0.4 ml) and 100 mg COH206 were dissolved in 0.3 M sodium phosphate buffer (pH 7.5) (0.4 ml). The two solutions were mixed and poured into a mold of approximately 5.0×0.5×0.2 cm. Gelation occurred in 2-3 minutes. The dried matrix is removed from the mold, and hydrated at 37° C. for one hour prior to the tensile strength test.

b. COH102/COH204: The sample is prepared as described in Example 5a, except that COH204 is substituted for COH206.

c. PE-4SHP/PE-3A: The sample is prepared by mixing 1.08 g of PE-4SHP, and 1.0 g of PE-3A in the presence of polyoxypropylene triamine (5-10 µg) (T403, Jeffamine, Texaco Chemical Co., Houston, Tex.), which serves as a base. All reactive species are liquids. 0.01% to 0.1% of fluorescein is added to the PE-4SHP prior to mixing the two components. Accordingly, PE-3A is warmed to 40° C. to form a liquid prior to mixing with PE-4SHP and T403 solution. Within 5 minutes after mixing, depending on the level of T403, gelation begins. The gel is allowed to cure for 20 minutes, followed by one hour of hydration at 37° C. Thereafter, the tensile strength of the gel is measured and fluorescence is observed by exciting with a light source.

d. Gelatin gels: 20% gelatin in sodium phosphate/sodium carbonate buffer (pH 9.6) having 0.1-1.0% fluorescein is mixed with different compounds as indicated and described in Example 5a, assuming 10-20 active amino groups per gelatin molecule, and using stoichiometric levels of the other compounds.

e. COH102/PPO-BA 2000/PEG-DA: 615 mg COH102 is dissolved in 0.9 ml ethanol, and mixed with 0.25 ml PPO-BA (MW=2,000) and 0.25 ml PEG-DA as described in Example 5a. Gelation occurs within 15 seconds and the gel becomes a firm, rubbery solid in two minutes or less.

f. PE-3A/PE-4SHP/PPO-BA 2,000: 0.5 ml PETA, 0.6 ml PE-4SHP and 0.15 ml PPO-BA 2,000 are mixed together as described in Example 5e with 0.01 to 0.1% fluorescein being added. Gelation occurs within two minutes and the gel becomes a firm, rubbery solid in ten minutes or less.

g. COH102/PTMO: The gel is prepared as described in Example 5e, with PTMO substituted for the PPO-BA 2,000.

h. Cyanoacrylate: Fluorescein is added to the glue, while it is extruded onto water where it immediately hardens.

i. HEMA: HEMA (1.3 ml) and PEG-DA (0.06 ml) were dissolved in of 150 mM sodium phosphate buffer (pH 7.4) (0.6 ml) to which 0.1% to 1.0% fluorescein is added, and mixed with a solution of 40 mg ammonium persulfate in 0.1 ml water. The was heated to 60-80° C. for 4 h while crosslinking occurred.

j. COH102/COH206/methylated collagen: 25 mg methylated collagen, 100 mg COH102 to which 0.1% to 1.0% fluorescein is added, and 100 mg COH206 are dissolved in 0.5 mM sodium phosphate (1 ml) (pH 6). The solution is co-extruded with a 0.3 M sodium phosphate/sodium carbonate buffer (1 ml) (pH 9.0). A gel is formed immediately.

Transient Colorant Activation and Tensile Strength Measurements:

The transient colorant in each of compositions 5a-j is activated by long wave uv light to observe bright yellow to green fluorescence. Then the ends of the dried gels are secured, and the central regions of all samples are rehydrated for approximately 1 hour in physiological saline buffer, pH 6.7 at 37° C. prior to the test. The matrices are extended to the point of breakage in an Instron Model 4202 test apparatus (Instron, Inc., Canton, Mass.) that is fitted with a 100 N load cell. The peak load is recorded and converted into ultimate stress using the measured cross-section of the sample at the break point. Data are also plotted as stress v. strain, using strain=$\Delta L/L_0$, where $\Delta L$ is the extension, and $L_0$ is the original sample length. The expected tensile strength measurements are observed that are similar to compositions not including the transient colorant.

What is claimed is:
1. A composition comprising:
(a) at least two polyethylene glycol (PEG) molecules each having a molecular weight in the range of about 7500 to about 20,000, wherein the PEG molecules include polymerizable groups; and
(b) an excitation agent that initiates polymerization of the at least two PEG molecules; and
(c) a colorant, wherein the colorant is non-reactive in the presence of the excitation agent and is visible or fluorescent in the presence of an excitation source and colorless in the absence of the excitation source.

2. The composition of claim 1, wherein the PEG has a molecular weight of approximately 10,000.

3. The composition of claim 1, wherein the PEG is activated PEG.

4. The composition of claim 3, wherein at least one of the at least two PEG molecules has a reactive electrophilic group.

5. The composition of claim 4, wherein the activated PEG has electrophilic groups selected from the group consisting of acid chloride groups, anhydrides, ketones, aldehydes, isocyanate, isothiocyanate, epoxides, and olefins.

6. The composition of claim 3, wherein the activated PEG is tetrafunctionally activated PEG.

7. The composition of claim 1, wherein the excitation agent is selected from the group consisting of moisture, a photopolymerization initiator, a catalyst, an agent that changes the pH of the composition, a basic reagent, a base, and a base-containing buffer.

8. The composition of claim 1, wherein the colorant is selected from the group consisting of a dye, a pigment, a luminescent agent, and mixtures thereof.

9. The composition of claim 8, wherein the colorant is a dye that includes a chromophore or a luminescent agent.

10. The composition of claim 8, wherein the colorant is a pigment that includes a chromophore or a luminescent agent.

11. The composition of claim 8, wherein the colorant is a fluorescent dye.

12. The composition of claim 11, wherein the fluorescent dye has an excitation wavelength from 300 nm to 700 nm.

13. The composition of claim 12, wherein the fluorescent dye is selected from the group consisting of fluorescein, carboxyfluorescein, eosin, erythrosine, a TEXAS RED® dye, rhodamine, coumarin, BODIPY® dye, or a combination thereof.

14. The composition of claim 1, further comprising at least one additional active component such as a small molecule therapeutic agent, a biopolymer, and a biological material.

15. The composition of claim 14, wherein the biopolymer is collagen or modified collagen.

16. The composition of claim 14, wherein the biological material is selected from the group consisting of tissue, cells, and mixtures thereof.

17. A composition comprising:
(a) a polyethylene glycol (PEG) with polymerizable groups;
(b) a poly(lysine);
(c) an excitation agent that initiates polymerization of the PEG and the poly(lysine); and
(d) a colorant, wherein the colorant is non-reactive in the presence of the excitation agent and is visible or fluorescent in the presence of an excitation source and colorless in the absence of the excitation source.

18. The composition of claim 17, wherein the PEG has a molecular weight in the range of approximately 7500 to 20,000.

19. The composition of claim 18, wherein the PEG has a molecular weight of about 10,000.

20. The composition of claim 17, wherein the poly(lysine) has a molecular weight in the range of about 8000 to about 15,000.

21. The composition of claim 17, wherein the excitation agent is selected from the group consisting of moisture, a photopolymerization initiator, a catalyst, an agent that changes the pH of the composition, a basic reagent, a base, and a base-containing buffer.

22. The composition of claim 17, wherein the colorant is selected from a dye, a pigment, a luminescent agent, and mixtures thereof.

23. The composition of claim 17, wherein the colorant is a dye that includes a chromophore or a luminescent agent.

24. The composition of claim 23, wherein the colorant is a pigment that includes a chromophore or a luminescent agent.

25. The composition of claim 22, wherein the colorant is a fluorescent dye.

26. The composition of claim 25, wherein the fluorescent dye has an excitation wavelength from 300 nm to 700 nm.

27. The composition of claim 26, wherein the fluorescent dye is selected from the group consisting of fluorescein, carboxyfluorescein, eosin, erythrosine, a TEXAS RED® dye, rhodamine, coumarin, BODIPY® dye, or a combination thereof.

28. The composition of claim 17, further comprising at least one additional active component such as a small molecule therapeutic agent, a biopolymer, and a biological material.

29. The composition of claim 28, wherein the biopolymer is collagen or modified collagen.

30. The composition of claim 28, wherein the biological material is selected from the group consisting of tissue, cells, and mixtures thereof.

31. The composition of claim 1, wherein at least one of the at least two PEG molecules has a nucleophilic group.

32. The composition of claim 1, wherein the excitation source is selected from the group consisting of visible light, ultraviolet light, electrical current, and laser stimulation.

33. The composition of claim 7, wherein the basic reagent is non-nucleophilic.

34. The composition of claim 7, wherein the excitation agent initiates polymerization of the at least two PEG molecules in the presence of the excitation source.

35. The composition of claim 15, wherein the modified collagen is methylated collagen.

36. The composition of claim 17, wherein the excitation source is selected from the group consisting of visible light, ultraviolet light, electrical current, and laser stimulation.

37. The composition of claim 17, wherein the poly(lysine) comprises 6 to about 4000 primary amino groups.

38. The composition of claim 21, wherein the basic reagent is non-nucleophilic.

39. The composition of claim 21, wherein the excitation agent initiates polymerization of the PEG and poly(lysine) in the presence of the excitation source.

40. The composition of claim 29, wherein the modified collagen is methylated collagen.

41. A method for visualizing, marking, or labeling a tissue surface comprising:
(a) applying to a tissue surface a biocompatible composition comprising a colorant and at least two polyethylene glycol (PEG) molecules each having a molecular weight in the range of about 7500 to about 20,000, wherein the PEG molecules include polymerizable groups; and
(b) applying to the tissue surface an excitation agent that initiates polymerization of the at least two PEG molecules,
wherein the colorant is non-reactive in the presence of the excitation agent and is visible or fluorescent in the presence of irradiation and colorless in the absence of irradiation.

42. The method of claim 41, wherein the PEG is activated PEG.

43. The method of claim 41, wherein the activated PEG is tetrafunctionally activated PEG.

44. The method of claim 41, wherein the excitation agent is selected from the group consisting of moisture, a photopolymerization initiator, a catalyst, an agent that changes the pH of the composition, a basic reagent, a base, and a base-containing buffer.

45. The method of claim 41, wherein the excitation agent initiates polymerization of the PEG and poly(lysine) in the presence of the excitation source.

46. The method of claim 41, wherein the colorant is selected from the group consisting of a dye, a pigment, a luminescent agent, and mixtures thereof.

47. The method of claim 41, wherein the excitation source is selected from the group consisting of visible light, ultraviolet light, electrical current, and laser stimulation.

48. The method of claim 41, further comprising at least one additional active component such as a small molecule therapeutic agent, a biopolymer, and a biological material.

49. The method of claim 48, wherein the biopolymer is collagen or modified collagen.

50. The method of claim 48, wherein the biological material is selected from the group consisting of tissue, cells, and mixtures thereof.

51. A method for visualizing, marking, or labeling a tissue surface comprising the steps of:
(a) applying to a tissue surface a biocompatible composition comprising a colorant, a polyethylene glycol (PEG) with polymerizable groups, and a poly(lysine) with polymerizable groups; and
(b) applying to the tissue surface an excitation agent that initiates polymerization of the at least two PEG molecules,
wherein the colorant is non-reactive in the presence of the excitation agent and is visible or fluorescent in the presence of irradiation and colorless in the absence of irradiation.

52. The method of claim 51, wherein the PEG has a molecular weight in the range of approximately 7500 to 20,000.

53. The method of claim 51, wherein the poly(lysine) has a molecular weight in the range of about 8000 to about 15,000.

54. The method of claim 51, wherein the poly(lysine) comprises 6 to about 4000 primary amino groups.

55. The method of claim 51, wherein the excitation agent is selected from the group consisting of moisture, a photopolymerization initiator, a catalyst, an agent that changes the pH of the composition, a basic reagent, a base, and a base-containing buffer.

56. The method of claim 51, wherein the excitation agent initiates polymerization of the PEG and the poly(lysine) in the presence of the excitation source.

57. The method of claim 51, wherein the colorant is selected from a dye, a pigment, a luminescent agent, and mixtures thereof.

58. The method of claim 51, wherein the excitation source is selected from the group consisting of visible light, ultraviolet light, electrical current, and laser stimulation.

59. The method of claim 51, further comprising at least one additional active component such as a small molecule therapeutic agent, a biopolymer, and a biological material.

60. The method of claim 59, wherein the biopolymer is collagen or modified collagen.

61. The method of claim 59, wherein the biological material is selected from the group consisting of tissue, cells, and mixtures thereof.

* * * * *